(12) United States Patent
Shida et al.

(10) Patent No.: US 11,965,817 B2
(45) Date of Patent: Apr. 23, 2024

(54) CELL CLASSIFICATION METHOD, CLASSIFICATION DEVICE, AND PROGRAM

(71) Applicant: SYSMEX CORPORATION, Kobe (JP)

(72) Inventors: Yuki Shida, Kobe (JP); Yukiko Nakamura, Kobe (JP); Ken Nishikawa, Kobe (JP); Kota Misawa, Kobe (JP); Hikaru Onoue, Kobe (JP); Takaaki Nagai, Kobe (JP); Masaki Abe, Kobe (JP); Takahito Mihara, Kobe (JP); Masaharu Shibata, Kobe (JP); Konobu Kimura, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 541 days.

(21) Appl. No.: 17/192,499

(22) Filed: Mar. 4, 2021

(65) Prior Publication Data

US 2021/0293692 A1    Sep. 23, 2021

(30) Foreign Application Priority Data

Mar. 19, 2020    (JP) ................................ 2020-049794

(51) Int. Cl.
*G01N 15/14*      (2006.01)
*G16B 5/00*      (2019.01)
(Continued)

(52) U.S. Cl.
CPC ........... *G01N 15/1475* (2013.01); *G16B 5/00* (2019.02); *G16B 50/00* (2019.02); *G01N 2015/008* (2013.01); *G16B 40/00* (2019.02)

(58) Field of Classification Search
CPC ......... G01N 15/1475; G01N 2015/008; G01N 35/04; G01N 2015/1402;
(Continued)

(56) References Cited

U.S. PATENT DOCUMENTS 9,568,488 B2    2/2017    Matsumoto et al.
10,775,379 B2    9/2020    Wu
(Continued)

FOREIGN PATENT DOCUMENTS

EP        1887357 A2    2/2008
JP    2008-008786 A    1/2008
(Continued)

OTHER PUBLICATIONS

Extended European search report dated Aug. 11, 2021 in European patent application No. 21157851.3.
(Continued)

*Primary Examiner* — Ali Bayat
(74) *Attorney, Agent, or Firm* — Crowell & Moring LLP

(57) ABSTRACT

Disclosed is a cell classification method, to be executed by an analyzer, for classifying cells contained in a specimen, including: preparing a first measurement sample by treating a specimen under a first preparation condition; obtaining a first signal from the prepared first measurement sample; classifying, by using the first signal, cells contained in the first measurement sample; preparing a second measurement sample by treating the specimen under a second preparation condition different from the first preparation condition; obtaining a second signal from the prepared second measurement sample; classifying, by using the second signal, cells contained in the second measurement sample; and comparing a result of the cell classification performed by using the first signal and a result of the cell classification performed by using the second signal, with each other, and outputting an analysis result including a number of cells on the basis of a result of the comparison.

20 Claims, 16 Drawing Sheets

(51) Int. Cl.
*G16B 50/00* (2019.01)
*G01N 15/00* (2006.01)
*G16B 40/00* (2019.01)

(58) Field of Classification Search
CPC ....... G01N 2035/0412; G01N 15/1459; G01N 15/10; G01N 2015/1006; G16B 5/00; G16B 50/00; G16B 40/00
USPC .......................................................... 382/133
See application file for complete search history.

(56) References Cited

U.S. PATENT DOCUMENTS

| | | | | |
|---|---|---|---|---|
| 2008/0019584 | A1* | 1/2008 | Lindberg | G06T 7/0012 382/134 |
| 2008/0082468 | A1* | 4/2008 | Long | G06V 10/764 706/12 |
| 2008/0308731 | A1* | 12/2008 | Nishiyama | H01J 37/20 250/440.11 |
| 2009/0248317 | A1 | 10/2009 | Nagai et al. | |
| 2012/0088230 | A1* | 4/2012 | Givens | G01N 21/648 435/7.1 |
| 2013/0273524 | A1* | 10/2013 | Ehrenkranz | G01N 21/8483 435/7.1 |
| 2016/0320381 | A1* | 11/2016 | Holmes | G01N 35/00069 |

FOREIGN PATENT DOCUMENTS

| | | |
|---|---|---|
| JP | 2016-514267 A | 5/2016 |
| WO | 2009/136570 A1 | 11/2009 |
| WO | 2014-143332 A1 | 9/2014 |

OTHER PUBLICATIONS

Japanese Office Action, dated Jan. 19, 2023, pp. 1-9, issued in Japanese patent application No. 2020-049794, Japan Patent Office, Chiyoda Tokyo, Japan.

* cited by examiner

PREPARATION CONDITION A

PREPARATION CONDITION B

CELL CLASSIFICATION METHOD, CLASSIFICATION DEVICE, AND PROGRAM

RELATED APPLICATIONS

This application claims priority to Japanese Patent Application No. 2020-049794, filed on Mar. 19, 2020, the entire content of which is incorporated herein by reference.

BACKGROUND OF THE INVENTION

1. Field of the Invention

The present invention relates to a cell classification method, a classification device, and a program.

2. Description of the Related Art

Technologies of classifying white blood cells in blood into a plurality of types by using information obtained by applying light to a sample that has been subjected to blood hemolysis, have been known. For example, Japanese Patent Application Publication No. 2016-514267 discloses a system in which a whole-blood measurement sample prepared according to a predetermined preparation condition is analyzed to identify, classify, and/or quantify white blood cells and subpopulations of the white blood cells in the sample.

In the system disclosed in Japanese Patent Application Publication No. 2016-514267, the measurement sample prepared according to the predetermined preparation condition is analyzed when white blood cells in blood are classified into the plurality of types. Meanwhile, there is a case where the white blood cells cannot be accurately classified depending on the property of a specimen. For example, there is a case where neutrophils and monocytes have substantially the same size and substantially the same membrane permeability for a staining liquid depending on the specimen, and in this case, the neutrophils and the monocytes cannot be accurately classified. However, in the system disclosed in Japanese Patent Application Publication No. 2016-514267, the measurement sample prepared according to the predetermined preparation condition is analyzed, and thus an analysis result with an insufficient accuracy is outputted depending on the property of the specimen.

SUMMARY OF THE INVENTION

The scope of the present invention is defined solely by the appended claims, and is not affected to any degree by the statements within this summary.

A cell classification method according to one aspect of the present invention is a cell classification method, to be executed by an analyzer (1), for classifying cells contained in a specimen. The cell classification method includes: preparing a first measurement sample by treating a specimen under a first preparation condition; obtaining a first signal from the prepared first measurement sample; classifying, by using the first signal, cells contained in the first measurement sample; preparing a second measurement sample by treating the specimen under a second preparation condition different from the first preparation condition; obtaining a second signal from the prepared second measurement sample; classifying, by using the second signal, cells contained in the second measurement sample; and comparing a result of the cell classification performed by using the first signal and a result of the cell classification performed by using the second signal, with each other, and outputting an analysis result including a number of cells on the basis of a result of the comparison. This makes it possible to inhibit an analysis result with an insufficient accuracy from being outputted depending on the property of the specimen.

A cell classification method according to another aspect of the present invention is a cell classification method, to be executed by an analyzer (1), for classifying cells contained in a specimen. The cell classification method includes: preparing a first measurement sample by treating a specimen under a first preparation condition; obtaining a first signal from the prepared first measurement sample; classifying, by using the first signal, cells contained in the first measurement sample; evaluating classification performance of the cell classification performed by using the first signal; and, if a result of the evaluation of the classification performance satisfies a predetermined condition, preparing a second measurement sample by treating the specimen under a second preparation condition different from the first preparation condition, obtaining a second signal from the prepared second measurement sample, classifying, by using the second signal, cells contained in the second measurement sample, and outputting a number of cells that is based on the second signal. This makes it possible to inhibit an analysis result with an insufficient accuracy from being outputted depending on the property of the specimen.

A cell classification method according to another aspect of the present invention is a cell classification method, to be executed by an analyzer (1), for classifying cells contained in a specimen. The cell classification method includes: preparing a first measurement sample by treating a specimen under a first preparation condition; obtaining a first signal from the prepared first measurement sample; classifying, by using the first signal, cells contained in the first measurement sample; preparing a second measurement sample by treating the specimen under a second preparation condition different from the first preparation condition; obtaining a second signal from the prepared second measurement sample; classifying, by using the second signal, cells contained in the second measurement sample; evaluating classification performance of the cell classification performed by using the first signal; and outputting, on the basis of a result of the evaluation of the classification performance, an analysis result including a number of cells that is based on the first signal or an analysis result including a number of cells that is based on the second signal. This makes it possible to inhibit an analysis result with an insufficient accuracy from being outputted depending on the property of the specimen.

An analyzer (1) according to another aspect of the present invention is an analyzer (1) configured to classify cells contained in a specimen. The analyzer (1) includes: a sample preparation part (25) configured to generate a measurement sample by preparation from a specimen with a reagent; a detector (26) configured to obtain a signal from a measurement sample; and a controller (500). The controller (500) is programmed to execute causing the sample preparation part (25) to execute preparing a first measurement sample by treating a specimen under a first preparation condition and preparing a second measurement sample by treating the specimen under a second preparation condition different from the first preparation condition; causing the detector (26) to execute obtaining a first signal from the prepared first measurement sample and obtaining a second signal from the prepared second measurement sample; classifying, by using the first signal, cells contained in the specimen; classifying, by using the second signal, cells contained in the specimen; and comparing a result of the cell classification performed by using the first signal and a result of the cell classification performed by using the second signal, with each other, and outputting an analysis result on the basis of a result of the comparison. This makes it possible to inhibit an analysis result with an insufficient accuracy from being outputted depending on the property of the specimen.

An analyzer (1) according to another aspect of the present invention is an analyzer (1) configured to classify cells contained in a specimen. The analyzer (1) includes: a sample preparation part (25) configured to generate a measurement sample by preparation from a specimen with a reagent; a detector (26) configured to obtain a signal from a measurement sample; and a controller (500). The controller (500) is programmed to execute causing the sample preparation part (25) to execute preparing a first measurement sample by treating a specimen under a first preparation condition and preparing a second measurement sample by treating the specimen under a second preparation condition different from the first preparation condition; causing the detector (26) to execute obtaining a first signal from the prepared first measurement sample; classifying, by using the first signal, cells contained in the specimen; evaluating classification performance of the cell classification performed by using the first signal; and if a result of the evaluation of the classification performance satisfies a predetermined condition, causing the sample preparation part (25) to execute preparing a second measurement sample by treating the specimen under a second preparation condition different from the first preparation condition, causing the detector (26) to execute obtaining a second signal from the prepared second measurement sample, classifying, by using the second signal, cells contained in the second measurement sample, and outputting a number of cells that is based on the second signal. This makes it possible to inhibit an analysis result with an insufficient accuracy from being outputted depending on the property of the specimen.

An analyzer (1) according to another aspect of the present invention is an analyzer (1) configured to classify cells contained in a specimen. The analyzer (1) includes: a sample preparation part (25) configured to generate a measurement sample by preparation from a specimen with a reagent; a detector (26) configured to obtain a signal from a measurement sample; and a controller (500). The controller (500) is programmed to execute causing the sample preparation part (25) to execute preparing a first measurement sample by treating a specimen under a first preparation condition and preparing a second measurement sample by treating the specimen under a second preparation condition different from the first preparation condition; causing the detector (26) to execute obtaining a first signal from the prepared first measurement sample and obtaining a second signal from the prepared second measurement sample; classifying, by using the first signal, cells contained in the specimen; classifying, by using the second signal, cells contained in the specimen; evaluating classification performance of the cell classification performed by using the first signal; and outputting, on the basis of a result of the evaluation of the classification performance, an analysis result including a number of cells that is based on the first signal or an analysis result including a number of cells that is based on the second signal. This makes it possible to inhibit an analysis result with an insufficient accuracy from being outputted depending on the property of the specimen.

A program according to another aspect of the present invention is configured to cause a computer to execute causing a sample preparation part (25), which is configured to generate a measurement sample by preparation from a specimen with a reagent, to execute preparing a first measurement sample by treating a specimen under a first preparation condition and preparing a second measurement sample by treating the specimen under a second preparation condition different from the first preparation condition; causing a detector (26), which is configured to obtain a signal from a measurement sample, to execute obtaining a first signal from the prepared first measurement sample and obtaining a second signal from the prepared second measurement sample; classifying, by using the first signal, cells contained in the specimen; classifying, by using the second signal, cells contained in the specimen; and comparing a result of the cell classification performed by using the first signal and a result of the cell classification performed by using the second signal, with each other, and outputting an analysis result on the basis of a result of the comparison. This makes it possible to inhibit an analysis result with an insufficient accuracy from being outputted depending on the property of the specimen.

A program according to another aspect of the present invention is configured to cause a computer to execute causing a sample preparation part (25), which is configured to generate a measurement sample by preparation from a specimen with a reagent, to execute preparing a first measurement sample by treating a specimen under a first preparation condition and preparing a second measurement sample by treating the specimen under a second preparation condition different from the first preparation condition; causing a detector (26), which is configured to obtain a signal from a measurement sample, to execute obtaining a first signal from the prepared first measurement sample; evaluating classification performance of the cell classification performed by using the first signal; and if a result of the evaluation of the classification performance satisfies a predetermined condition, causing the sample preparation part (25) to execute preparing a second measurement sample by treating the specimen under a second preparation condition different from the first preparation condition, causing the detector (26) to execute obtaining a second signal from the prepared second measurement sample, classifying, by using the second signal, cells contained in the second measurement sample, and outputting a number of cells that is based on the second signal. This makes it possible to inhibit an analysis result with an insufficient accuracy from being outputted depending on the property of the specimen.

A program according to another aspect of the present invention is configured to cause a computer to execute causing a sample preparation part (25), which is configured to generate a measurement sample by preparation from a specimen with a reagent, to execute preparing a first measurement sample by treating a specimen under a first preparation condition and preparing a second measurement sample by treating the specimen under a second preparation condition different from the first preparation condition; causing a detector (26), which is configured to obtain a signal from a measurement sample, to execute obtaining a first signal from the prepared first measurement sample and obtaining a second signal from the prepared second measurement sample; classifying, by using the first signal, cells contained in the specimen; classifying, by using the second signal, cells contained in the specimen; evaluating classification performance of the cell classification performed by using the first signal; and outputting, on the basis of a result of the evaluation of the classification performance, an analysis result including a number of cells that is based on the first signal or an analysis result including a number of cells that is based on the second signal. This makes it possible to inhibit an analysis result with an insufficient accuracy from being outputted depending on the property of the specimen.

According to the present invention, it is possible to inhibit an analysis result with an insufficient accuracy from being outputted depending on the property of the specimen.

DETAILED DESCRIPTION OF THE PREFERRED EMBODIMENTS

Figure 1:
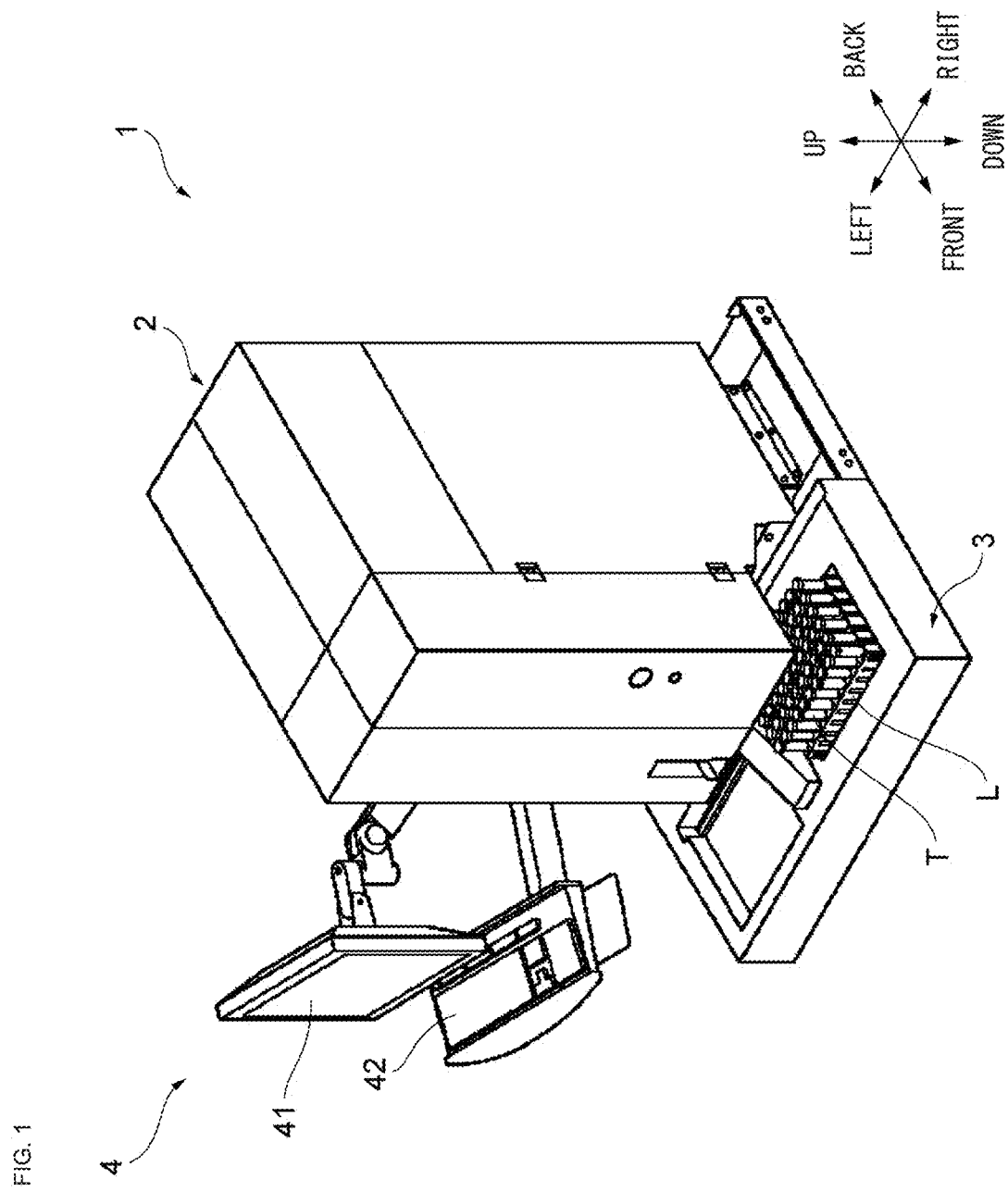
FIG. 1 is a perspective view showing the appearance of an analyzer according to the present embodiment.

An embodiment of the present disclosure will be described with reference to the attached drawings. In the drawings, components denoted by the same reference characters have the same or similar configurations.
<Configuration of Specimen Measurement System>

FIG. 1 is a perspective view showing the appearance of an analyzer 1 according to the present embodiment. The analyzer 1 is a multi-item blood cell analyzer that counts blood cells, i.e., white blood cells contained in a blood specimen. The analyzer 1 includes: a measurement unit 2; a transport unit 3 disposed on the front side of the measurement unit 2; and an information processing unit 4. A blood specimen that is peripheral blood collected from a patient is contained in a specimen container (blood collection tube) T. A plurality of the specimen containers T are supported on a sample rack L. The sample rack L is transported by the transport unit 3, and each of the blood specimens is supplied to the measurement unit 2.

Figure 2:
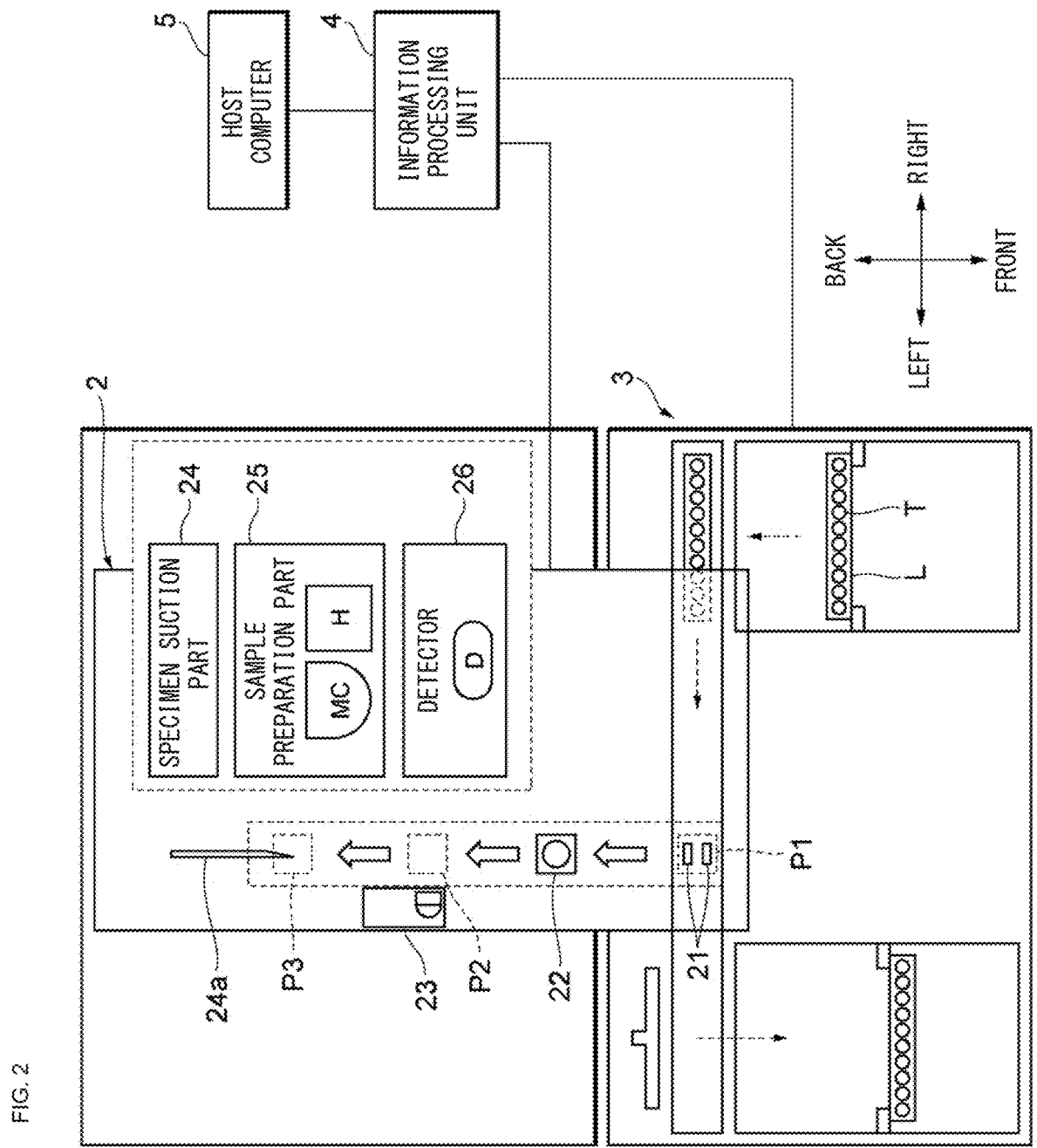
FIG. 2 schematically illustrates an example of a configuration of a measurement unit.

The information processing unit 4 includes a display part 41 and an input part 42 and is communicably connected to the measurement unit 2, the transport unit 3, and a host computer 5 (see FIG. 2). The information processing unit 4 controls operations of the measurement unit 2 and the transport unit 3, performs analysis on the basis of the result of measurement performed by the measurement unit 2, and transmits the result of the analysis to the host computer 5 (see FIG. 2).

FIG. 2 schematically illustrates an example of a configuration of the measurement unit 2.

The measurement unit 2 includes a hand part 21, a specimen container setting part 22, a bar code unit 23, a specimen suction part 24, a sample preparation part 25, and a detector 26. The specimen suction part 24 includes a piercer 24a and suctions a specimen from each of the specimen containers T. The sample preparation part 25 includes a mixing chamber MC and a heater H. The sample preparation part 25 mixes a reagent with the specimen, to prepare a measurement sample that is used for measurement. The detector 26 includes an optical detector D and detects blood cells from the measurement sample. Each of the components of the measurement unit 2 is controlled by the information processing unit 4.

Each specimen container T positioned at a position P1 by the transport unit 3 is gripped by the hand part 21 and pulled out upward from the sample rack L. Then, the hand part 21 is swung so that the specimen in the specimen container T is agitated. The specimen container T for which agitation has been finished is set, by the hand part 21, to the specimen container setting part 22 positioned at the position P1. Thereafter, the specimen container T is transported to a position P2 by the specimen container setting part 22.

When the specimen container T is positioned at the position P2, the bar code unit 23 disposed near the position P2 reads a specimen number from a bar code label pasted on the specimen container T. Thereafter, the specimen container T is transported to a position P3 by the specimen container setting part 22. When the specimen container T is positioned at the position P3, a predetermined amount of the specimen is suctioned from the specimen container T via the piercer 24a by the specimen suction part 24. When suction of the specimen is finished, the specimen container T is transported frontward by the specimen container setting part 22 and returned to the original support position on the sample rack L by the hand part 21. After the piercer 24a is transferred to a position in the mixing chamber MC, a predetermined amount of the specimen suctioned via the piercer 24a is discharged into the mixing chamber MC by the specimen suction part 24.

The sample preparation part 25 mixes the blood specimen and a reagent with each other according to a predetermined preparation condition, to prepare a measurement sample. The reagent contains a hemolytic agent (first reagent) and a fluorescent substance (second reagent). Red blood cells and platelets in the blood are hemolyzed with the hemolytic agent, and white blood cells in the blood are stained with the fluorescent substance.

The measurement sample prepared by the sample preparation part 25 is supplied to the optical detector D of the detector 26.

Figure 3:
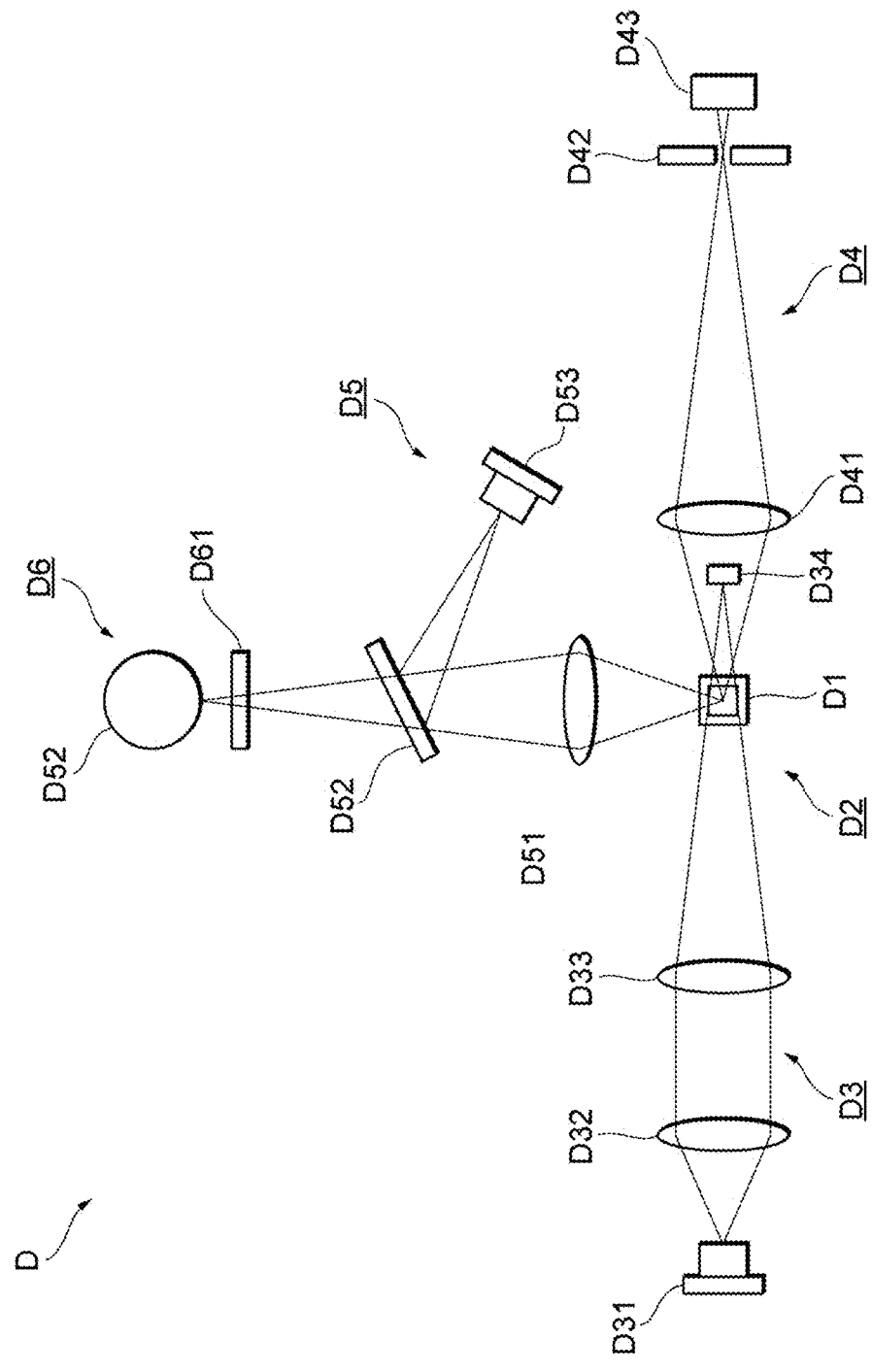
FIG. 3 schematically illustrates an example of a configuration of an optical detector.

FIG. 3 schematically illustrates an example of a configuration of the optical detector D. The optical detector D includes a flow cell D1, a sheath flow system D2, a beam spot forming system D3, a forward scattered light receiving system D4, a side scattered light receiving system D5, and a fluorescence receiving system D6.

The sheath flow system D2 is configured to send the measurement sample into the flow cell D1 and generate a liquid flow in the flow cell D1. The beam spot forming system D3 is configured such that light emitted from a semiconductor laser D31 passes through a collimator lens D32 and a condenser lens D33 and is applied to the flow cell D1. Thus, the laser light is applied to blood cells contained in the liquid flow passing through the inside of the flow cell D1. In addition, the beam spot forming system D3 further includes a beam stopper D34.

The forward scattered light receiving system D4 is configured to condense scattered light advancing forward (forward scattered light) by a forward condenser lens D41 and receive light, which has passed through a pinhole D42, by a photodiode D43. The photodiode D43 outputs a forward scattered light signal (FSC) on the basis of a peak value of the received forward scattered light. The side scattered light receiving system D5 is configured to condense scattered light advancing sideways (side scattered light) by a side condenser lens D51, reflect a portion of the light by a dichroic mirror D52, and receive the portion by a photodiode D53. The photodiode D53 outputs a side scattered light signal (SSC) on the basis of a peak value of the received side scattered light.

Light scattering is a phenomenon that occurs when the advancing direction of light is changed owing to the presence of a particle such as a blood cell as an obstacle in the advancing direction of the light. If the scattered light is detected, information about the size and the material properties of the particle can be obtained. In particular, information about the size of the particle (blood cell) can be obtained from forward scattered light. Further, information about the inside of the particle can be obtained from side scattered light. If laser light is applied to a blood cell particle, the intensity of the side scattered light is dependent on the complexity (the shape, the size, and the density of the nucleus and the amount of granules) inside the cell.

The fluorescence receiving system D6 is configured to allow a light (fluorescence), which has been transmitted through the dichroic mirror D52, of the side scattered light to further pass through a spectral filter D61; and receive the fluorescence by an avalanche photodiode D62. The avalanche photodiode D62 outputs a side fluorescence signal (SFL) on the basis of a peak value of the received fluorescence.

When light is applied to a blood cell stained with the fluorescent substance, a fluorescence having a wavelength longer than the wavelength of the applied light is emitted. The intensity of the fluorescence increases if the blood cell is well stained. Measurement of the intensity of the fluorescence makes it possible to obtain information about the extent to which the blood cell is stained.

The forward scattered light signal (FSC), the side scattered light signal (SSC), and the side fluorescence signal (SFL) obtained from each blood cell by the optical detector D are transmitted to the information processing unit 4.

Figure 4:
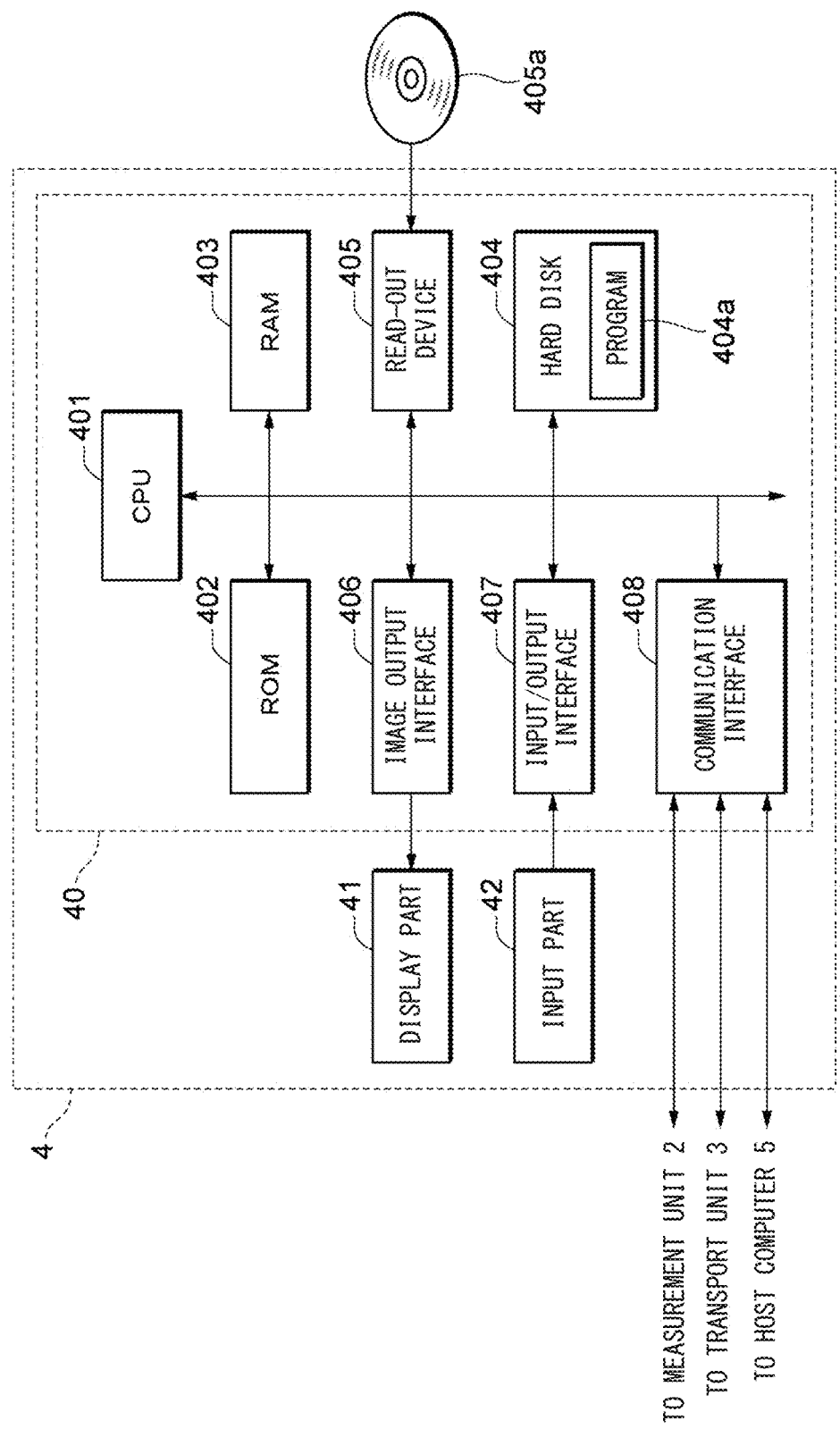
FIG. 4 illustrates an example of a configuration of an information processing unit.

FIG. 4 illustrates an example of a configuration of the information processing unit 4.

The information processing unit 4 is implemented by a personal computer and includes a body 40, the display part 41, and the input part 42. The body 40 includes a CPU 401, a ROM 402, a RAM 403, a hard disk 404, a read-out device 405, an image output interface 406, an input/output interface 407, and a communication interface 408.

The CPU 401 executes a computer program stored in the ROM 402 and a computer program loaded to the RAM 403. The RAM 403 is used for reading out computer programs recorded in the ROM 402 and the hard disk 404. In addition, the RAM 403 is used also as a work area for the CPU 401 when these computer programs are executed.

The hard disk 404 stores an operating system, a computer program to be executed by the CPU 401, and data used for executing the computer program. In addition, the hard disk 404 stores a program 404a for executing a process for the information processing unit 4. The read-out device 405 is implemented by a CD drive, a DVD drive, or the like, and can read out a computer program and data recorded in a non-transitory computer readable recording medium 405a. If the above program 404a is recorded in the recording medium 405a, the program 404a having been read out from the recording medium 405a by the read-out device 405 is stored in the hard disk 404.

The image output interface 406 outputs, to the display part 41, a video signal corresponding to image data. The display part 41 displays an image on the basis of the video signal outputted from the image output interface 406. A user inputs an instruction through the input part 42. The input/output interface 407 receives a signal inputted through the input part 42. The communication interface 408 is connected to the measurement unit 2, the transport unit 3, and the host computer 5, and the CPU 401 transmits/receives an instruction signal and data to/from these devices via the communication interface 408.

Figure 5:
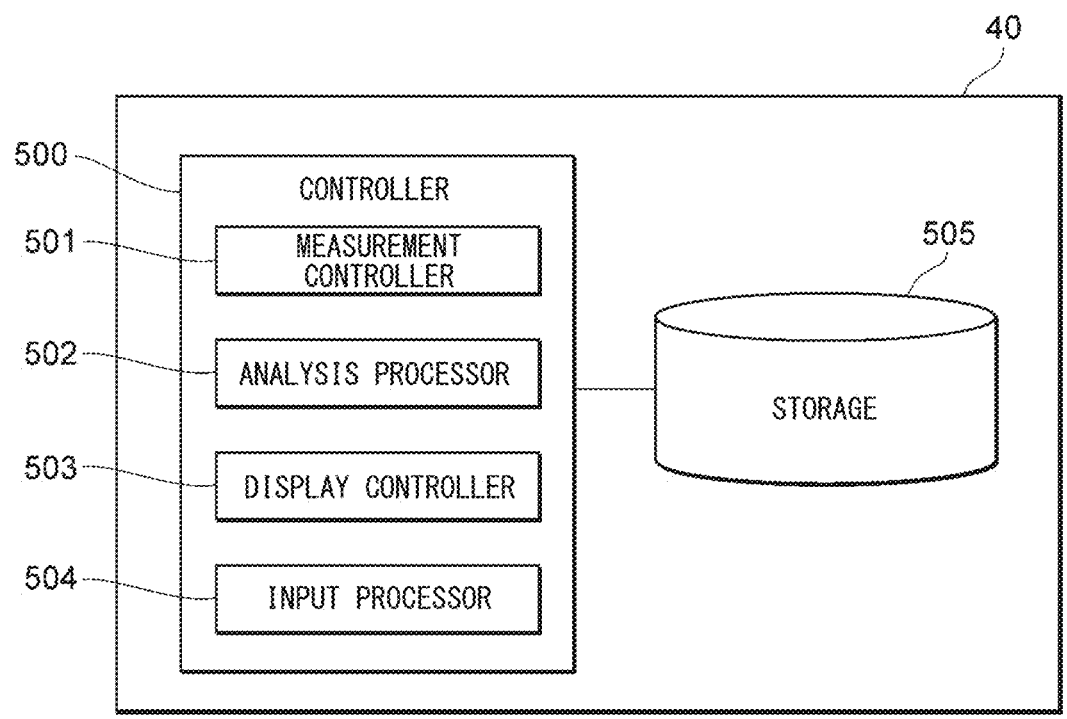
FIG. 5 illustrates an example of a functional configuration of the information processing unit.

FIG. 5 illustrates an example of a functional configuration of the information processing unit 4. A controller 500 is implemented through read-out and execution of a computer program by the CPU 401. A storage 505 is implemented by using the RAM 403 or the hard disk 404.

The controller 500 includes: a measurement controller 501 configured to measure a specimen by controlling operations of the measurement unit 2 and the transport unit 3; an analysis processor 502 configured to, for example, classify white blood cells and count the number of blood cells on the basis of forward scattered light signals (FSC), side scattered light signals (SSC), and side fluorescence signals (SFL) measured by the detector 26 of the measurement unit 2; a display controller 503 configured to perform processing of displaying a measured number of blood cells in each type of white blood cell, a scattergram (distribution chart), etc., on the display part 41; and an input processor 504 configured to receive an input from the user through the input part 42.

The storage 505 stores, for each blood cell, measurement information received from the measurement unit 2 and indicating the level of a forward scattered light signal (FSC), the level of a side scattered light signal (SSC), and the level of a side fluorescence signal (SFL). The measurement information expresses each of the level of the forward scattered light signal (FSC), the level of the side scattered light signal (SSC), and the level of the side fluorescence signal (SFL) by a quantized value called a "channel". The channel will be described later.

The analysis processor 502 classifies, on the basis of the measurement information stored in the storage 505, white blood cells existing in the blood specimen into lymphocyte (LYMPH), monocyte (MONO), neutrophil (NEUT), basophil (BASO), and eosinophil (EO). The analysis processor 502 counts the number of blood cells in each of the classified types.

The analysis processor 502 creates a scattergram (distribution chart) on the basis of the measurement information, to classify the white blood cells existing in the blood specimen.

Here, the scattergram is a two-dimensional distribution chart in which two types of signals out of the forward scattered light signal (FSC) outputted from the photodiode D43, the side scattered light signal (SSC) outputted from the photodiode D53, and the side fluorescence signal (SFL) outputted from the avalanche photodiode D62 are used as a vertical axis and a horizontal axis.

The types of white blood cells that can be classified differ depending on the two types of signals to be used out of the forward scattered light signal (FSC), the side scattered light signal (SSC), and the side fluorescence signal (SFL). In the present embodiment, four types of white blood cells, i.e., neutrophils, lymphocytes, monocytes, and eosinophils are classified by using the side fluorescence signal (SFL) and the side scattered light signal (SSC). Alternatively, basophils and white blood cells other than basophils (neutrophils, lymphocytes, monocytes, and eosinophils) can be classified by using the forward scattered light signal (FSC) and the side fluorescence signal (SFL).

Figure 6:
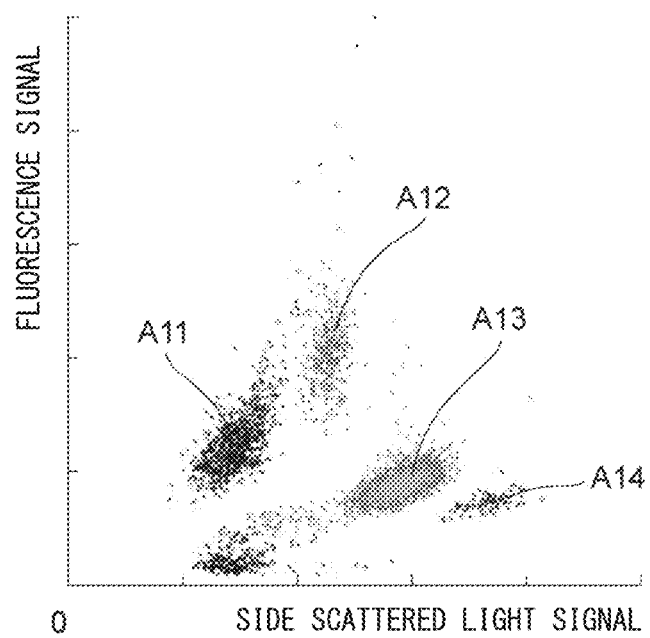
FIG. 6 illustrates an example of a scattergram.

The scattergram shown in FIG. 6 is an example of the case where dots corresponding to individual blood cells are plotted on a two-dimensional distribution chart in which the side scattered light signal (SSC) is used as a horizontal axis and the side fluorescence signal (SFL) is used as a vertical axis. The blood cells can be classified by the same method as the following method also in the case where basophils and white blood cells other than the basophils are classified by using the forward scattered light signal (FSC) and the side fluorescence signal (SFL) as two axes.

The analysis processor 502 classifies each of the dots on the scattergram into any of four clusters corresponding to the four respective subclasses of white blood cells (a cluster A11 of lymphocytes, a cluster A12 of monocytes, a cluster A13 of neutrophils, and a cluster A14 of eosinophils). Specifically, for example, the belonging degrees of each of the blood cells to the clusters are obtained from the distances between a dot plotted on the scattergram and corresponding to the blood cell and the positions of preset centers of gravity of the clusters. Then, the blood cell is assigned to a corresponding cluster according to the belonging degrees.

Here, an example of the procedure of assigning each blood cell to a corresponding cluster will be more specifically described. Two types of signals used for creating a scattergram are amplified by an amplifier and then converted into digital signals by an A/D converter. That is, quantization is performed. By this quantization, each of the signals is classified into any of, for example, a total of 256 channels from 0 to 255.

Figure 7:
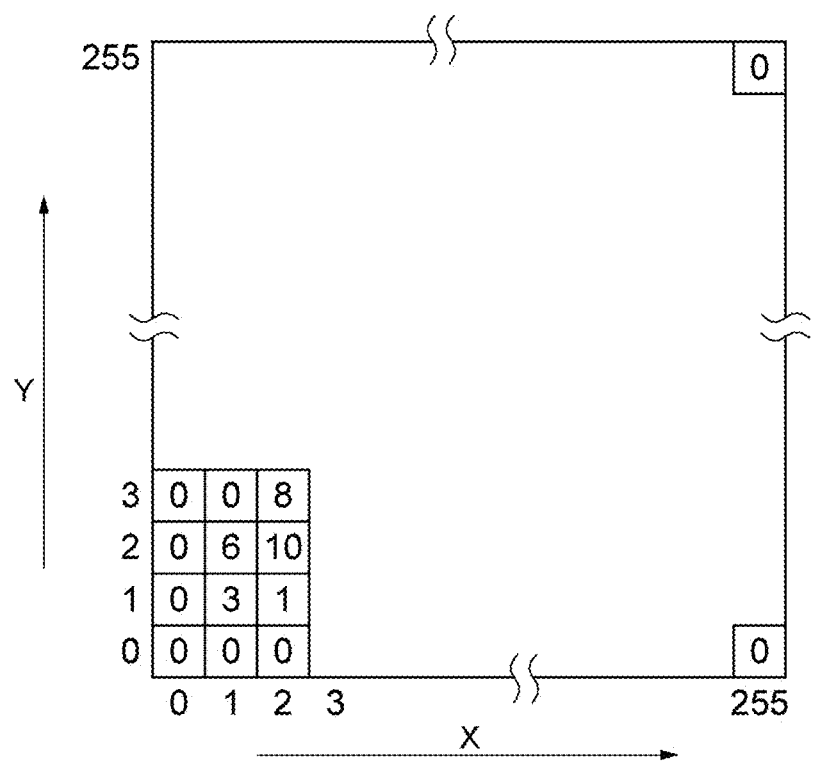
FIG. 7 illustrates an example of a distribution of blood cells in the scattergram.

The information processing unit 4 obtains, on the basis of these digital signals, a scattergram in which i-channels are used for an X-axis and j-channels are used for a Y-axis as shown in FIG. 7. In the scattergram, each of the X-axis and the Y-axis has 256 channels. Thus, the scattergram is composed of a total of 256×256 basic elements indicating the states of blood cells. Each of the basic elements stores the number of blood cells corresponding to the basic element. For example, if the value of a basic element at channel 1 in the X-axis and channel 2 in the Y-axis is 6, the value indicates that there are six blood cells for each of which the intensity of a signal indicating the size of the cytoplasm of the blood cell is 1; and the intensity of a composite signal indicating the densities and the sizes of the nucleus and granules of the blood cell is 2.

Figure 8:
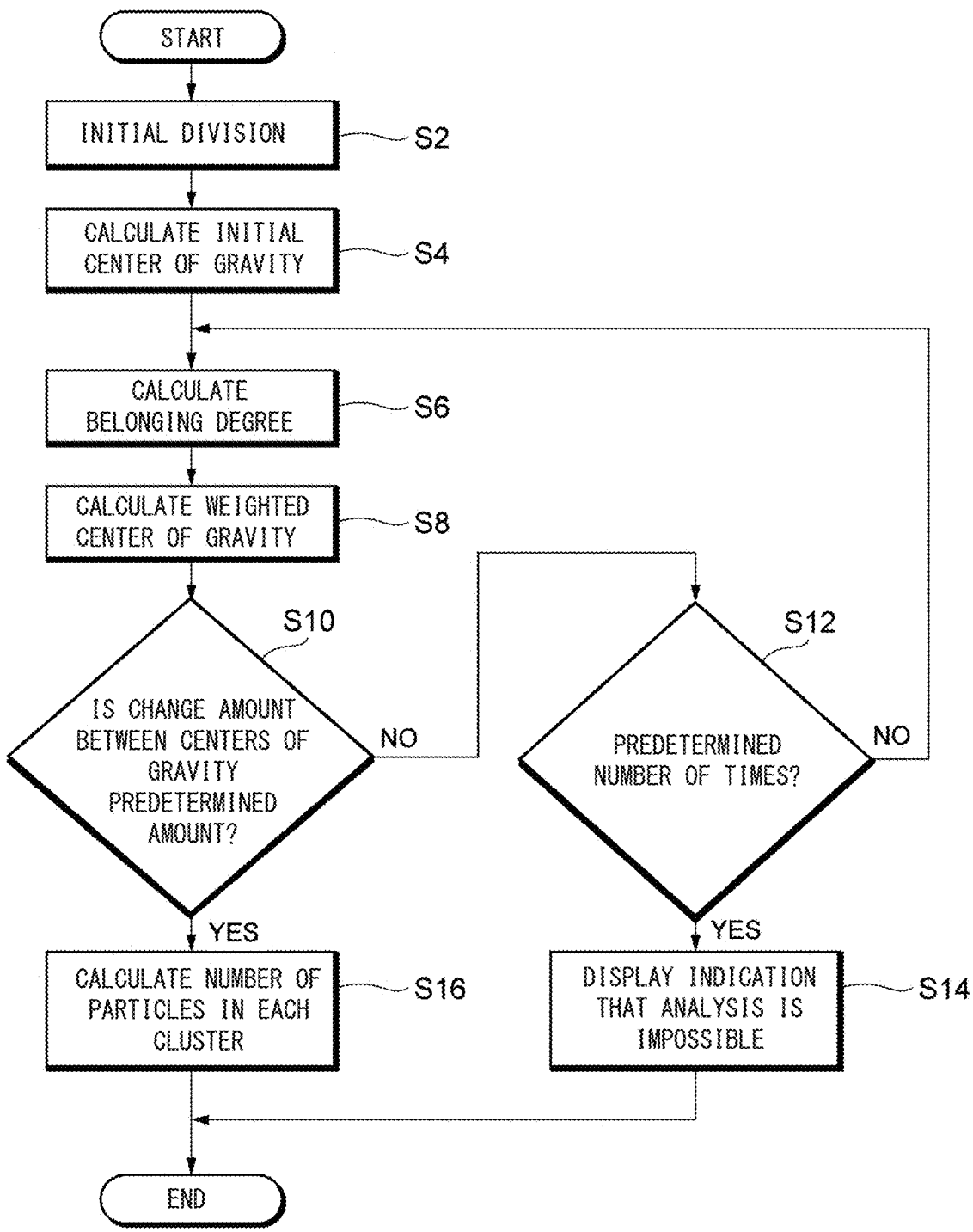
FIG. 8 is a flowchart showing an example of processing of assigning each blood cell to any of clusters.

FIG. 8 is a flowchart showing an example of processing of assigning each blood cell to any of the clusters. First, the information processing unit 4 performs initial division (S2). The initial division is performed as follows while the number of blood cells in each of the basic elements of the scattergram shown in FIG. 7 is ignored. For lymphocytes, the distribution of the basic elements is divided by a fixed region in which the lymphocytes are assumed to be obviously distributed. For monocytes, the distribution of the basic elements is divided by a fixed region in which the monocytes are assumed to be obviously distributed. For neutrophils, the distribution of the basic elements is divided by a fixed region in which the neutrophils are assumed to be obviously distributed. For eosinophils, the distribution of the basic elements is divided by a fixed region in which the eosinophils are assumed to be obviously distributed. For ghosts including platelets and red blood cells, the distribution of the basic elements is divided by a fixed region in which the ghosts are assumed to be obviously distributed. Each of the fixed regions is preset. The belonging degree of each of the blood cells existing in a corresponding fixed region is defined as 1.

Subsequently, the information processing unit 4 calculates an initial center of gravity of the cluster of lymphocytes by using the following Mathematical expression 1 and Mathematical expression 2 (S4).

$$X_{G1} = \sum_i \sum_j N_{ij} \cdot i \bigg/ \sum_i \sum_j N_{ij} \quad \text{[Mathematical expression 1]}$$

$$Y_{G1} = \sum_i \sum_j N_{ij} \cdot i \bigg/ \sum_i \sum_j N_{ij} \quad \text{[Mathematical expression 2]}$$

Here, $N_{ij}$ is the number of blood cells at a basic element i, j. The positions of centers of gravity are obtained in the same manner as for the clusters of monocytes, neutrophils, eosinophils, and ghosts.

Subsequently, the information processing unit 4 calculates the belonging degrees, to the clusters, of each of blood cells that do not belong to any of the fixed regions (S6). More specifically, the information processing unit 4 calculates the belonging degrees to the clusters on the basis of the distances from the position of each of the blood cells to the positions of the centers of gravity of the clusters. Here, the distance from the position of the blood cell to each of the positions of the centers of gravity of the clusters is not the distance (Euclidean distance) between the position of the blood cell and the position of the cluster, but the length of the minor axis of a predetermined ellipse is defined as the distance between the position of the blood cell and the position of the cluster. The predetermined ellipse refers to an ellipse that has a center at the position of the center of gravity of a cluster and that has a specific tilt having been set in advance according to the cluster. A given blood cell is positioned on the arc of the ellipse. If the minor axis of the ellipse is defined as "a", the major axis thereof is represented by "ak" ("k" is a coefficient of proportionality).

If the distances $L_x$ (x=1 to N ("N" is the number of clusters)) from each blood cell to the clusters are obtained, the belonging degrees of the blood cell to the clusters are obtained according to Mathematical expression 3. As a matter of course, each of the belonging degrees is a value smaller than 1.

$$\text{Belonging degree} = \frac{\frac{1}{L_x}}{\frac{1}{L_1} + \frac{1}{L_2} + \ldots + \frac{1}{L_N}} \quad \text{[Mathematical expression 3]}$$

In this manner, the information processing unit 4 calculates the belonging degrees, to the clusters, of each blood cell that does not belong to any of the fixed regions.

Subsequently, for each of the clusters, the belonging degree of each blood cell to the cluster is used as a weight to calculate a weighted center of gravity (S8). The weighted center of gravity is obtained according to, for example, Mathematical expression 4 and Mathematical expression 5.

$$X'_{G1} = \sum_i \sum_j Uij \cdot Nij \cdot i \Big/ \sum_i \sum_j Uij \cdot Nij \quad \text{[Mathematical expression 4]}$$

$$Y'_{G1} = \sum_i \sum_j Uij \cdot Nij \cdot j \Big/ \sum_i \sum_j Uij \cdot Nij \quad \text{[Mathematical expression 5]}$$

Here, $U_{ij}$ represents the belonging degree of a blood cell at a basic element i, j to a certain cluster G1.

After the weighted center of gravity of each cluster is obtained in this manner, the weighted center of gravity is compared with a corresponding one of the positions of the initial centers of gravity of the clusters obtained in step S4, and whether the change amount therebetween is a predetermined amount, e.g. 0, is determined (S10). If the change amount is not the predetermined amount, the position of the presently-obtained weighted center of gravity of the cluster is used in place of the initial center of gravity of the cluster, and the processing procedures of steps S6, S8, and S10 are repeated. That is, the distances from the position of each blood cell to the positions of the weighted centers of gravity of the clusters are obtained; the belonging degrees of the blood cell to the clusters are obtained on the basis of the distances; the positions of weighted centers of gravity of the clusters are newly obtained on the basis of the belonging degrees; and whether the change amount between each of the positions of the new weighted centers of gravity of the clusters and the position of the previous weighted center of gravity of the cluster is the predetermined amount, is determined. If the change amount is not the predetermined amount again, the position of the presently-obtained weighted center of gravity of the cluster is set as the position of an initial center of gravity thereof, and the processing procedures of steps S6, S8, and S10 are repeated.

However, a case is assumed in which the change amount does not become the predetermined amount even if steps S6, S8, and S10 are repeated a predetermined number of times. Thus, if the determination in step S10 is NO, the information processing unit 4 determines whether the number of times of execution of steps S6, S8, and S10 is the predetermined number of times (S12). If the number reaches the predetermined number of times, the information processing unit 4 displays, on the display part 41, an indication that analysis is impossible (S14), and ends the processing.

Meanwhile, if the change amount between the centers of gravity of each cluster becomes the predetermined amount, the information processing unit 4 determines final belonging of each blood cell to a corresponding cluster, to determine the number of blood cells in each cluster (step S16).

Regarding the final belonging of each blood cell, the blood cell may be regarded as belonging to a cluster in which the blood cell has a maximum value out of the finally obtained belonging degrees. For example, if ten blood cells are present in a certain basic element, the belonging degree of each of these blood cells to the cluster of lymphocytes is 0.95, the belonging degree thereof to the cluster of monocytes is 0.03, the belonging degree thereof to the cluster of neutrophils is 0.03, the belonging degree thereof to the cluster of eosinophils is 0.02, and the belonging degree thereof to the cluster of ghosts is 0, all of these ten blood cells are regarded as belonging to the cluster of lymphocytes in which the blood cells have the maximum belonging degree.

By performing the above processing, each blood cell existing in the scattergram is assigned to any of the clusters.

<Operation of Analyzer>

The analyzer 1 first performs processing of classifying white blood cells and counting the number of blood cells with use of a measurement sample prepared according to a predetermined preparation condition; and outputting an analysis result. This processing is referred to as a "normal mode" in the present embodiment. If the analyzer 1 determines that the white blood cells may not have been sufficiently classified in the normal mode, the analyzer 1 performs processing of preparing a measurement sample under a different preparation condition; classifying white blood cells and counting the number of blood cells again; and outputting an analysis result. This processing is referred to as an "extension mode" in the present embodiment.

Figure 9:
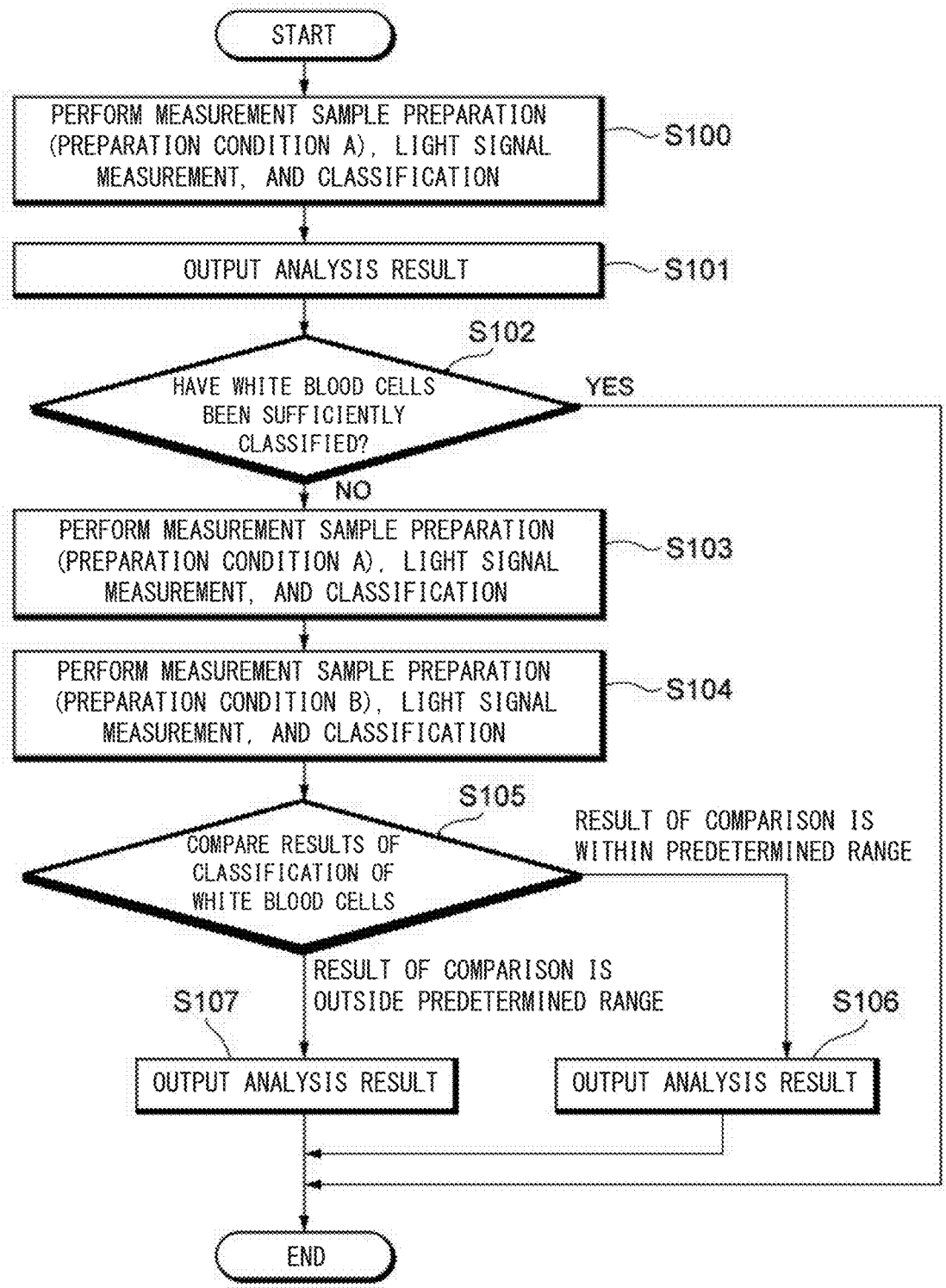
FIG. 9 is a flowchart showing an example of processing procedures to be executed by an analyzer.

FIG. 9 is a flowchart showing an example of processing procedures to be executed by the analyzer 1.

In step S100, the sample preparation part 25 of the measurement unit 2 mixes a blood specimen and a reagent with each other according to a predetermined preparation condition, to prepare a measurement sample. Hereinafter, the predetermined preparation condition is referred to as "preparation condition A".

Preparation condition A (the same applies to preparation condition B described below) is a condition regarding a time length during which the reagent is reacted with the blood specimen. Preparation condition A (the same applies to preparation condition B described below) may be at least either one condition among a condition regarding the temperature when the reagent is reacted with the blood specimen and a condition regarding the mixing ratio between the blood specimen and the reagent. The condition regarding the time length during which the reagent is reacted with the blood specimen, may be a condition regarding a time length of heating when the blood specimen and the reagent are blended and heated by a heater.

The reaction time, the temperature, and the mixing ratio in preparation condition A are set in advance to a value that allows white blood cells to be classified into lymphocytes, monocytes, neutrophils, basophils, and eosinophils in the case of a healthy blood specimen.

Subsequently, the detector 26 of the measurement unit 2 applies light (laser light) to the prepared measurement sample, to obtain light signals. Subsequently, the controller 500 of the information processing unit 4 classifies white blood cells contained in the blood specimen on the basis of the light signals and counts the number of blood cells in each type of white blood cell.

In step S101, the controller 500 of the information processing unit 4 outputs a scattergram and/or the number of blood cells in each type of white blood cell as the result of classification of the white blood cells.

In step S102, the controller 500 evaluates, for the measurement sample prepared according to preparation condition A, classification performance regarding classification of white blood cells (cell classification), to determine whether or not the white blood cells have been sufficiently separated. The classification performance means an index indicating the extent of accuracy with which a plurality of types of cells have been classified. More specifically, the classification performance means an index indicating that the blood specimen has been accurately classified into the types of white blood cells (lymphocytes, monocytes, neutrophils, basophils, and eosinophils) by analyzing the light signals. For example, if at least any two types of white blood cells among lymphocytes, monocytes, neutrophils, basophils, and eosinophils have not been sufficiently separated as a result of classifying white blood cells, the controller 500 determines that the white blood cells have not been sufficiently classified.

If the controller 500 determines that the white blood cells have been sufficiently classified (may be rephrased as "if the classification performance does not satisfy a predetermined condition"), the controller 500 ends the processing without performing transition to the extension mode. Meanwhile, if the controller 500 determines that the white blood cells may not have been sufficiently classified (may be rephrased as "if the classification performance satisfies the predetermined condition"), the controller 500 proceeds to the processing procedure of step S103 in order to perform transition to the extension mode. The case where the white blood cells may not have been sufficiently classified is considered to occur if, for example, an unhealthy blood specimen such as blood collected from a subject who suffers from a certain disease is analyzed.

In step S103, the sample preparation part 25 of the measurement unit 2 mixes the blood specimen and the reagent with each other according to preparation condition A again, to prepare a measurement sample. Subsequently, the detector 26 of the measurement unit 2 applies light to the prepared measurement sample, to obtain light signals. Subsequently, the controller 500 of the information processing unit 4 classifies white blood cells contained in the blood specimen by using the light signals and counts the number of blood cells in each type of white blood cell.

In step S104, the sample preparation part 25 of the measurement unit 2 mixes the blood specimen and the reagent with each other according to preparation condition B different from preparation condition A, to prepare a measurement sample. Subsequently, the detector 26 of the measurement unit 2 applies light to the prepared measurement sample, to obtain light signals. Subsequently, the controller 500 of the information processing unit 4 classifies white blood cells contained in the blood specimen by using the light signals and counts the number of blood cells in each type of white blood cell.

In step S105, the controller 500 compares the result of the classification of the white blood cells performed by using the light signals obtained under preparation condition A and the result of the classification of the white blood cells performed by using the light signals obtained under preparation condition B. If the result of the comparison between the result of the classification under preparation condition A and the result of the classification under preparation condition B is within a predetermined range, the controller 500 determines that the white blood cells have been sufficiently classified under preparation condition A, and proceeds to the processing procedure of step S106. Meanwhile, if the result of the comparison is outside the predetermined range, the controller 500 determines that the white blood cells have been more appropriately classified in the result of the classification under preparation condition B than in the result of the classification under preparation condition A, and proceeds to the processing procedure of step S107.

In step S106, the controller 500 outputs an analysis result including the number of blood cells in each type of white blood cell on the basis of the result of the comparison in step S105. More specifically, the controller 500 outputs the counted number of each type of white blood cell and/or a scattergram that are based on the light signals obtained under preparation condition A.

In step S107, the controller 500 outputs an analysis result including the number of blood cells in each type of white blood cell on the basis of the result of the comparison in step S105. For example, the controller 500 outputs, to the display part 41, the counted number of each type of white blood cell and/or a scattergram that are based on the light signals obtained under preparation condition A and information about the reliability of the counted number of each type of white blood cell. The information about the reliability may be, for example, a flag or a character string indicating that the counted number of each type of white blood cell and/or the scattergram has low reliability.

In each of the processing procedures of step S100, step S103, and step S104 described above, the controller 500 classifies white blood cells by using two light signals, i.e., the side fluorescence signal (SFL) and the side scattered light signal (SSC) which are emitted from measurement sample A (or measurement sample B). White blood cells may be classified by using at least two light signals among two types of scattered lights (that is, the forward scattered light signal (FSC) and the side scattered light signal (SSC)) each having a different angle, and the side fluorescence signal (SFL).

The controller 500 obtains the result of classification of white blood cells on the basis of a scattergram obtained by plotting, in different axes, two light signals, i.e., the side fluorescence signal (SFL) and the side scattered light signal (SSC).

The controller 500 obtains, by using the side fluorescence signal (SFL) and the side scattered light signal (SSC), a classification result in which the blood specimen is classified into four types, i.e., lymphocyte, monocyte, neutrophil, and eosinophil.

Alternatively, the controller 500 may obtain, by using all of the forward scattered light signal (FSC), the side scattered light signal (SSC), and the side fluorescence signal (SFL), a classification result in which the blood specimen is classified into five types, i.e., lymphocyte, monocyte, neutrophil, basophil, and eosinophil.

Preparation condition A, the measurement sample, and the light signals in the processing procedure of step S103 described above are referred to as a first preparation condition, a first measurement sample, and first light signals, respectively. Further, preparation condition B, the measurement sample, and the light signals in the processing procedure of step S104 are referred to as a second preparation condition, a second measurement sample, and second light signals, respectively. Further, preparation condition A, the measurement sample, and the light signals in the processing procedure of step S100 are referred to as a third preparation condition, a third measurement sample, and third light signals, respectively.

As another example, preparation condition A, the measurement sample, and the light signals in the processing procedure of step S100 are referred to as the first preparation condition, the first measurement sample, and the first light signals, respectively. Further, preparation condition B, the measurement sample, and the light signals in the processing procedure of step S104 are referred to as the second preparation condition, the second measurement sample, and the second light signals, respectively.

In the above embodiment, preparation of a sample under preparation condition A, light signal measurement, and classification, are executed in step S100 and step S103. Consequently, even if a long time elapses from the sample preparation in step S100 until the sample preparation in step S103, the sample preparation under preparation condition A is performed by using a sample in a state that is similar to the state of a sample to be prepared according to preparation condition B in step S104. Therefore, the accuracy of the analysis result to be outputted in step S106 or step S107 can be improved.

(Modification 1 Regarding Operation of Analyzer)

The controller 500 outputs, in the processing procedure of step S107, the counted number of each type of white blood cell and/or a scattergram that are based on the light signals obtained under preparation condition B.

(Modification 2 Regarding Operation of Analyzer)

The controller 500 may not perform the processing procedures of step S103 and step S105 out of the processing procedures shown in FIG. 9. That is, if an evaluation result obtained by evaluating the classification performance for white blood cells for which the light signals obtained under preparation condition A have been used satisfies the predetermined condition, the controller 500 executes the processing procedure of step S104 without executing the processing procedure of step S103. Further, the controller 500 classifies white blood cells contained in the blood specimen by using the light signals that have been obtained under preparation condition B and that have been obtained in the processing procedure of step S104, counts the number of each type of blood cells, and outputs the counted number of each type of white blood cell and/or a scattergram to the display part 41.

In modification 2, preparation condition A, the measurement sample, and the light signals in the processing procedure of step S100 are referred to as the first preparation condition, the first measurement sample, and the first light signals, respectively. Further, preparation condition B, the measurement sample, and the light signals in the processing procedure of step S104 are referred to as the second preparation condition, the second measurement sample, and the second light signals, respectively.

(Modification 3 Regarding Operation of Analyzer)

The controller 500 receives a measurement instruction, to measure the blood specimen not in the normal mode but in the extension mode, from a user through the input part 42. In this case, when the controller 500 receives the measurement instruction, the controller 500 does not perform the processing procedures of step S100 to step S102 out of the processing procedures shown in FIG. 9 (that is, the normal mode is not used).

(Modification 4 Regarding Operation of Analyzer)

The controller 500 performs processing in which modification 1 and modification 3 described above are combined with each other. That is, if the controller 500 receives, from the user, the measurement instruction to measure the blood specimen not in the normal mode but in the extension mode, the controller 500 does not perform the processing procedures of step S100 to step S102 out of the processing procedures shown in FIG. 9 (that is, the normal mode is not used). In addition, in the processing procedure of step S107, the counted number of each type of white blood cell and/or a scattergram that are based on the light signals obtained under preparation condition B is outputted.

<Examples of Preparation Condition A and Preparation Condition B>

Preparation condition B is a condition in which the time during which the reagent is reacted with the blood specimen is set to be longer than that in preparation condition A. Alternatively, preparation condition B may be a condition in which the temperature when the reagent is reacted with the blood specimen is set to be higher than that in preparation condition A. Alternatively, preparation condition B may be a condition in which, regarding the mixing ratio between the blood specimen and the reagent, the proportion of the reagent is set to be higher than that in preparation condition A.

<Specific Examples of Processing of Performing Determination or Analysis for Result of Classification of White Blood Cells>

Specific description will be given regarding processing of determining whether or not the white blood cells have been sufficiently classified (S102) in processing of determining whether or not to perform transition from the normal mode to the extension mode; and processing of outputting, in the extension mode, an analysis result through comparison between the result of classification of white blood cells under preparation condition A and the result of classification of white blood cells under preparation condition B (S105 to S107).

(Pattern A)

Pattern A is a method in which the number of cells belonging to one cluster among a plurality of clusters existing in a scattergram is used to perform determination or comparison for the results of classification of white blood cells.

[Processing of Determining Necessity of Transition from Normal Mode to Extension Mode]

If the counted number of white blood cells belonging to one cluster is a predetermined value (for example, 0) or is equal to or smaller than a predetermined value (for example, 5, 10, or the like) as a result of classifying white blood cells, the controller 500 determines that the white blood cells may not have been sufficiently classified (that is, determines that the classification performance satisfies the predetermined condition). Meanwhile, if the counted numbers of all types of white blood cells are values other than the predetermined value (for example, 0) or are equal to or larger than the predetermined value, the controller 500 determines that the white blood cells have been sufficiently classified (that is, determines that the classification performance does not satisfy the predetermined condition).

As an example, if the counted number of eosinophils is the predetermined value (for example, 0) as a result of classifying white blood cells into four types of white blood cells, i.e., neutrophils, lymphocytes, monocytes, and eosinophils, by using the side fluorescence signal (SFL) and the side scattered light signal (SSC) as light signals, the controller 500 determines that the white blood cells have not been sufficiently classified.

[Processing of Comparing Classification Results Under Preparation Condition A and Preparation Condition B with Each Other]

The controller 500 outputs an analysis result including the number of blood cells in each type of white blood cell on the basis of the result of the comparison between the number of cells belonging to one cluster among a plurality of clusters included in a scattergram obtained under preparation condition A and the number of cells belonging to the one cluster among a plurality of clusters included in a scattergram obtained under preparation condition B.

More specifically, if the difference between the number of white blood cells belonging to one cluster among a plurality of clusters included in a scattergram obtained under preparation condition A and the number of white blood cells belonging to the one cluster among a plurality of clusters included in a scattergram obtained under preparation condition B is within a predetermined range, the controller 500 determines that the white blood cells have been sufficiently classified under preparation condition A, and proceeds to the processing procedure of step S106. Meanwhile, if this difference is outside the predetermined range, the controller 500 determines that the white blood cells have been more appropriately classified in the result of the classification under preparation condition B than in the result of the classification under preparation condition A, and proceeds to the processing procedure of step S107.

Figure 10A:
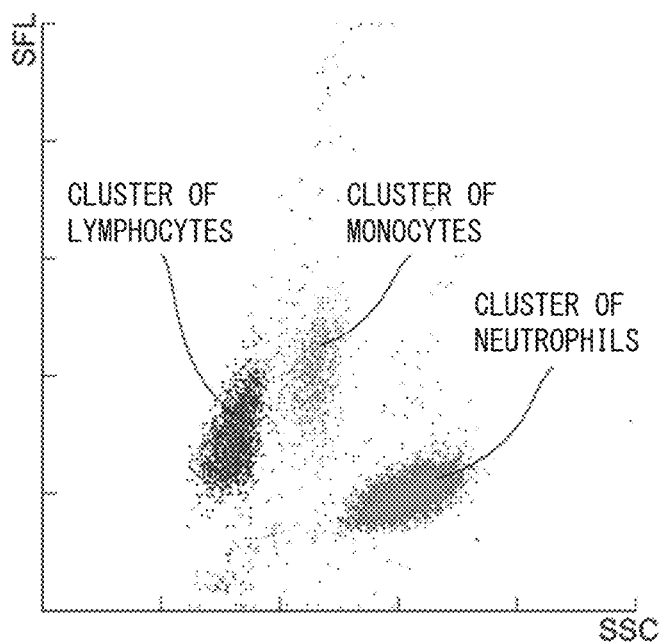
FIG. 10A illustrates an example of the result of classification under preparation condition A.
Figure 10B:
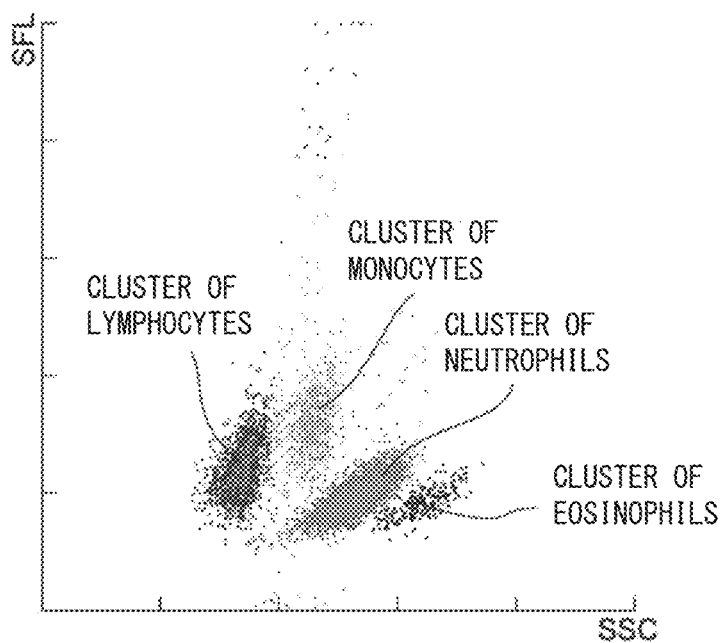
FIG. 10B illustrates an example of the result of classification under preparation condition B.

FIG. 10A illustrates an example of the result of the classification under preparation condition A, and FIG. 10B illustrates an example of the result of the classification under preparation condition B. In the examples in FIG. 10A and FIG. 10B, no cluster of eosinophils exists (the number of eosinophils is 0) in the result of the classification under preparation condition A, but a cluster of eosinophils exists (the number of eosinophils is equal to or larger than 100) in the result of the classification under preparation condition B. Therefore, the controller 500 determines that the white blood cells have been more appropriately classified in the result of the classification under preparation condition B than in the result of the classification under preparation condition A.

(Pattern B)

Pattern B is a method in which the number of clusters existing in a scattergram is used to perform determination or comparison for the results of classification of white blood cells.

[Processing of Determining Necessity of Transition from Normal Mode to Extension Mode]

If the number of clusters existing in a scattergram is smaller than a predetermined value as a result of classifying white blood cells, the controller 500 determines that the white blood cells may not have been sufficiently classified (that is, determines that the classification performance satisfies the predetermined condition). Meanwhile, if the number of clusters is the predetermined value, the controller 500 determines that the white blood cells have been sufficiently classified (that is, determines that the classification performance does not satisfy the predetermined condition). The predetermined value is set in advance according to the type of the scattergram. For example, in the case of a scattergram in which the side fluorescence signal (SFL) is used as a Y-axis and the side scattered light signal (SSC) is used as an X-axis, the predetermined value is four types (neutrophil, lymphocyte, monocyte, and eosinophil).

[Processing of Comparing White Blood Cell Classification Results Under Preparation Condition A and Preparation Condition B with Each Other]

The controller 500 outputs an analysis result including the number of blood cells in each type of white blood cell on the basis of the result of the comparison between the number of clusters existing in a scattergram obtained under preparation condition A and the number of clusters existing in a scattergram obtained under preparation condition B.

More specifically, if the difference between the number of clusters existing in a scattergram obtained under preparation condition A and the number of clusters existing in a scattergram obtained under preparation condition B is within a predetermined range (for example, the difference is 0), the controller 500 determines that the white blood cells have been sufficiently classified under preparation condition A, and proceeds to the processing procedure of step S106. Meanwhile, if this difference is outside the predetermined range (for example, the difference is equal to or larger than 1), the controller 500 determines that the white blood cells have been more appropriately classified in the result of the classification under preparation condition B than in the result of the classification under preparation condition A, and proceeds to the processing procedure of step S107.

In the examples in FIG. 10A and FIG. 10B, only three clusters exist in the result of the classification under preparation condition A, but four clusters exist in the result of the classification under preparation condition B. Therefore, the controller 500 determines that the white blood cells have been more appropriately classified in the result of the classification under preparation condition B than in the result of the classification under preparation condition A.

(Pattern C)

Pattern C is a method in which the distance between two clusters included in a scattergram is used to perform determination or comparison for the results of classification of white blood cells.

[Processing of Determining Necessity of Transition from Normal Mode to Extension Mode]

If the distance between two clusters existing in a scattergram is equal to or smaller than a predetermined value as a result of classifying white blood cells, the controller 500 determines that the white blood cells may not have been sufficiently classified (that is, determines that the classification performance satisfies the predetermined condition). Meanwhile, if the distance between the two clusters is larger than the predetermined value, the controller 500 determines that the white blood cells have been sufficiently classified (that is, determines that the classification performance does not satisfy the predetermined condition).

As an example, if the distance between a cluster of neutrophils and a cluster of monocytes is equal to or smaller than a predetermined value, the controller 500 determines that the white blood cells have not been sufficiently classified.

[Processing of Comparing White Blood Cell Classification Results Under Preparation Condition A and Preparation Condition B with Each Other]

The controller 500 outputs an analysis result including the number of blood cells in each type of white blood cell on the basis of the result of the comparison between the distance between two clusters included in a scattergram obtained under preparation condition A and the distance between the two clusters included in a scattergram obtained under preparation condition B.

More specifically, if the difference between the distance between predetermined two clusters included in a scattergram obtained under preparation condition A and the distance between the predetermined two clusters included in a scattergram obtained under preparation condition B is within a predetermined range (for example, equal to or shorter than 10 channels or the like), the controller 500 determines that the white blood cells have been sufficiently classified under preparation condition A, and proceeds to the processing procedure of step S106. Meanwhile, if this difference is outside the predetermined range (for example, in the case of being longer than 10 channels, or the like), the controller 500 determines that the white blood cells have been more appropriately classified in the result of the classification under preparation condition B than in the result of the classification under preparation condition A, and proceeds to the processing procedure of step S107.

Figure 11A:
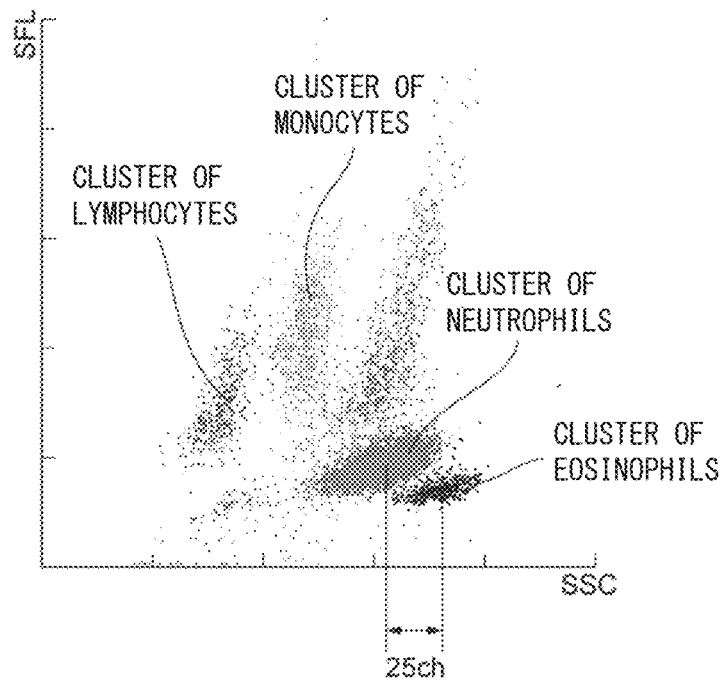
FIG. 11A illustrates an example of the result of classification under preparation condition A.
Figure 11B:
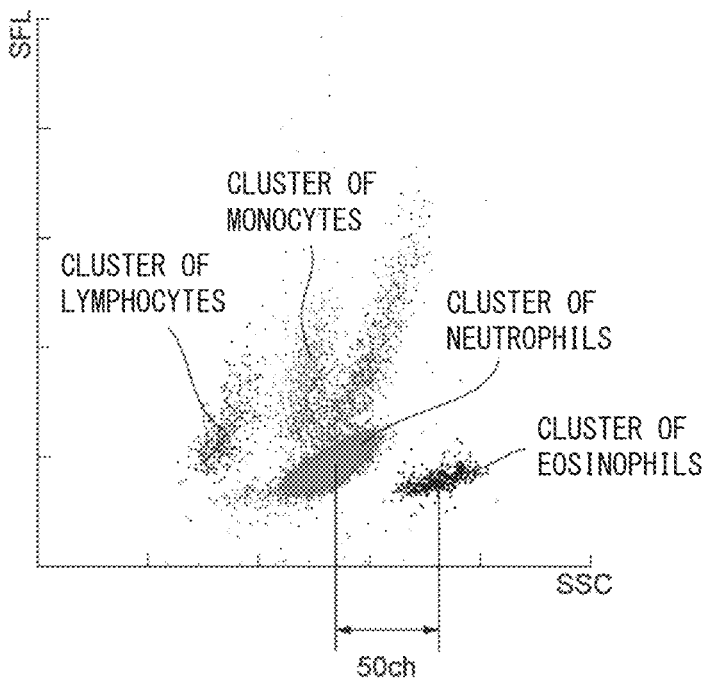
FIG. 11B illustrates an example of the result of classification under preparation condition B.

In the examples in FIG. 11A and FIG. 11B, the distance between a cluster of neutrophils and a cluster of eosinophils is 25 channels in the result of the classification under preparation condition A, but the distance between the cluster of neutrophils and the cluster of eosinophils is 50 channels in the result of the classification under preparation condition B. In this case, the difference between the distances between the clusters is 25 channels and outside the predetermined range (10 channels). Therefore, the controller 500 determines that the white blood cells have been more appropriately classified in the result of the classification under preparation condition B than in the result of the classification under preparation condition A.

The distance between clusters may be obtained by comparing the average values, in the X-axis, of the positions of blood cells belonging to the clusters, with each other. Here, the average value, in the X-axis, of the positions of blood cells belonging to each of the clusters can be calculated by dividing the total value of the X-axis values (channel values) of the blood cells by the number of the blood cells. For example, in the case where a cluster enclosed by a region with X=0 to 2 and Y=0 to 3 is assumed to exist as shown in FIG. 7, the average value in the X-axis is ((3+6)×1+(1+10+8)×2)÷(3+6+1+10+8)≈1.68. The distance between clusters is not limited thereto and may be obtained by comparing the average values, in the Y-axis, of the positions of blood cells belonging to the clusters, with each other.

In pattern C, the two clusters, the distances between which are to be compared with each other, may be set in advance according to the type of the scattergram. For example, in the case of a scattergram in which the side fluorescence signal (SFL) is used as a Y-axis and the side scattered light signal (SSC) is used as an X-axis, the distances between a cluster of lymphocytes and a cluster of monocytes may be set to be compared with each other, the distances between the cluster of monocytes and a cluster of neutrophils may be set to be compared with each other, or the distances between the cluster of neutrophils and a cluster of eosinophils may be set to be compared with each other.

(Pattern D)

Pattern D is a method in which the extent to which the boundaries of two clusters existing in a scattergram are in contact with each other is used to perform determination or comparison for the results of classification of white blood cells.

[Processing of Determining Necessity of Transition from Normal Mode to Extension Mode]

If the extent to which the boundaries of two clusters existing in a scattergram are in contact with each other is equal to or smaller than a predetermined value as a result of classifying white blood cells, the controller 500 determines that the white blood cells may not have been sufficiently classified (that is, determines that the classification performance satisfies the predetermined condition). Meanwhile, if the extent to which the boundaries of the two clusters are in contact with each other is larger than the predetermined value, the controller 500 determines that the white blood cells have been sufficiently classified (that is, determines that the classification performance does not satisfy the predetermined condition).

[Processing of Comparing Classification Results Under Preparation Condition A and Preparation Condition B with Each Other]

The controller 500 outputs an analysis result including the number of blood cells in each type of white blood cell on the basis of the result of the comparison between the extent to which the boundaries of two clusters included in a scattergram obtained under preparation condition A are in contact with each other and the extent to which the boundaries of the two clusters included in a scattergram obtained under preparation condition B are in contact with each other.

More specifically, if the difference between the extent to which the boundaries of two clusters included in a scattergram obtained under preparation condition A are in contact with each other and the extent to which the boundaries of the two clusters included in a scattergram obtained under preparation condition B are in contact with each other is within a predetermined range, the controller 500 determines that the white blood cells have been sufficiently classified under preparation condition A, and proceeds to the processing procedure of step S106. Meanwhile, if this difference is outside the predetermined range, the controller 500 determines that the white blood cells have been more appropriately classified in the result of the classification under preparation condition B than in the result of the classification under preparation condition A, and proceeds to the processing procedure of step S107.

Figure 12A:
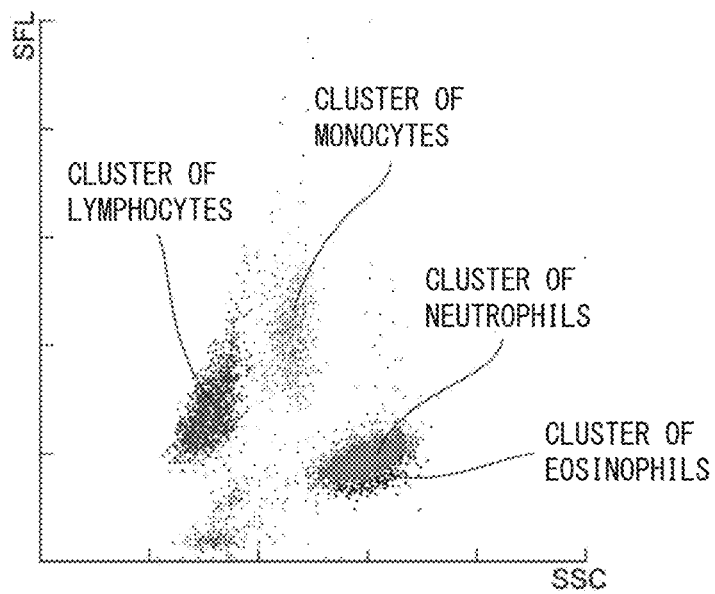
FIG. 12A illustrates an example of the result of classification under preparation condition A.
Figure 12B:
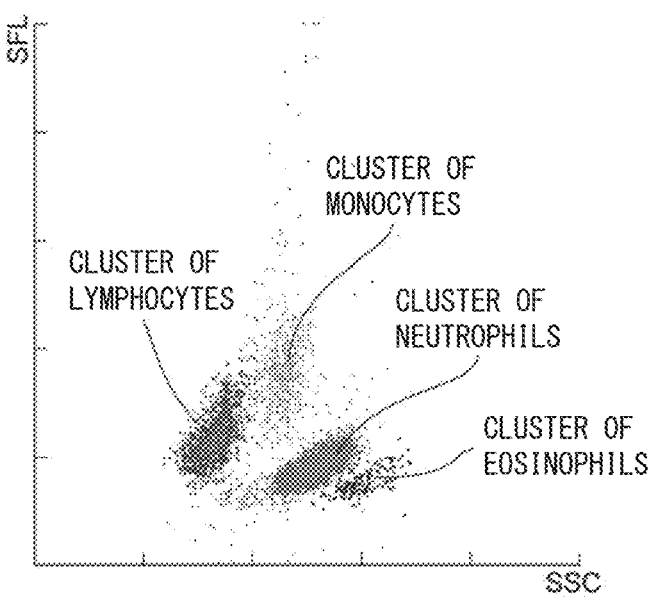
FIG. 12B illustrates an example of the result of classification under preparation condition B.

FIG. 12A illustrates an example of the result of the classification under preparation condition A, and FIG. 12B illustrates an example of the result of the classification under preparation condition B. In the examples in FIG. 12A and FIG. 12B, a cluster of neutrophils and a cluster of eosinophils are in contact with each other in the result of the classification under preparation condition A, but the cluster of neutrophils and the cluster of eosinophils are not in contact with each other in the result of the classification under preparation condition B. Therefore, the controller 500 determines that the white blood cells have been more appropriately classified in the result of the classification under preparation condition B than in the result of the classification under preparation condition A.

Figure 13A:
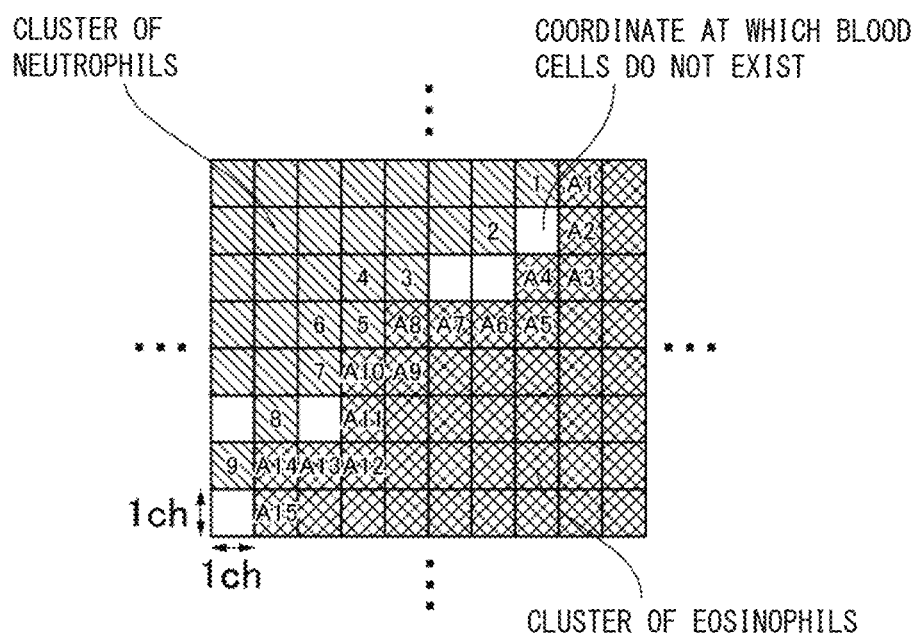
FIG. 13A illustrates an example of calculation of the extent to which the boundaries of two clusters are in contact with each other.
Figure 13B:
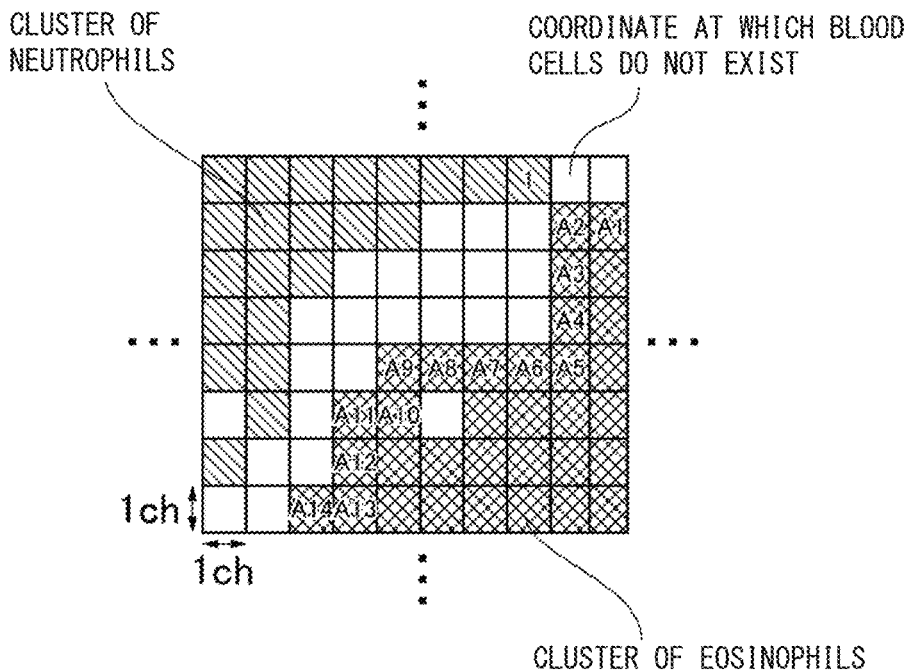
FIG. 13B illustrates an example of the calculation of the extent to which the boundaries of the two clusters are in contact with each other.

FIG. 13A illustrates an example of calculation of the extent to which the boundaries of two clusters are in contact with each other. FIG. 13B illustrates an example of the calculation of the extent to which the boundaries of the two clusters are in contact with each other. FIG. 13A and FIG. 13B are enlarged diagrams of areas in which the cluster of neutrophils and the cluster of eosinophils are in contact with each other in the scattergrams. The vertical direction is an axis (Y-axis) based on the side fluorescence signal (SFL), and the horizontal direction is an axis (X-axis) based on the side scattered light signal (SSC).

The extent to which the boundaries of two clusters are in contact with each other is a value obtained by counting the number of coordinates, among coordinates existing around each coordinate on the boundary of either one cluster out of the two clusters, at which blood cells belonging to the other cluster exist. For example, in the case of FIG. 13A, among eight coordinates around a coordinate of A4, the coordinate at which neutrophils exist is one coordinate on the upper left side of the coordinate of A4. Similarly, among eight coordinates around a coordinate of A8, the coordinates at which neutrophils exist are three coordinates on the left, upper left, and upper sides of the coordinate of A8. By thus performing counts, in the case of FIG. 13A, the extent to which the boundaries of the cluster of neutrophils and the cluster of eosinophils are in contact with each other is "9". In the case of FIG. 13B, the extent to which the boundaries of the cluster of neutrophils and the cluster of eosinophils are in contact with each other is "1".

Although the coordinates at which neutrophils exist among the coordinates around the cluster of eosinophils are counted in the examples in FIG. 13A and FIG. 13B, the number of coordinates may be counted on the basis of the cluster of neutrophils. For example, the number of coordinates at which eosinophils exist among coordinates existing around each coordinate on the boundary of the cluster of neutrophils, is counted.

In pattern D, the two clusters, the contact extents of which are to be compared with each other, may be set in advance according to the type of the scattergram. For example, in the case of a scattergram in which the side fluorescence signal (SFL) is used as a Y-axis and the side scattered light signal (SSC) is used as an X-axis, the extents to which a cluster of lymphocytes and a cluster of monocytes are in contact with each other may be compared with each other, the extents to which the cluster of monocytes and a cluster of neutrophils are in contact with each other may be compared with each other, or the extents to which the cluster of neutrophils and a cluster of eosinophils are in contact with each other may be compared with each other.

(Pattern E)

Pattern E is a method in which the distribution shape of blood cells of a cluster existing in a scattergram is used to perform determination or comparison for the results of classification of white blood cells.

[Processing of Determining Necessity of Transition from Normal Mode to Extension Mode]

If the distribution shape of blood cells, in the X-axis or the Y-axis, of at least one cluster existing in a scattergram satisfies a predetermined condition as a result of classifying white blood cells, the controller 500 determines that the white blood cells may not have been sufficiently classified (that is, determines that the classification performance satisfies the predetermined condition). Meanwhile, if the distribution shape of the blood cells, in the X-axis or the Y-axis, of the at least one cluster existing in the scattergram does not satisfy the predetermined condition, the controller 500 determines that the white blood cells have been sufficiently classified (that is, determines that the classification performance does not satisfy the predetermined condition).

The predetermined condition may be that two or more peaks exist when the numbers of blood cells existing in respective channels in the X-axis are represented by a histogram. Here, the method for calculating the numbers of the blood cells existing in the respective channels in the X-axis will be described with reference to FIG. 7. For example, a cluster enclosed by the region with X=0 to 2 and Y=0 to 3 is assumed to exist. In this case, the numbers of blood cells in respective channels of X=0, 1, and 2 are 0, 9, and 19, respectively.

[Processing of Comparing Classification Results Under Preparation Condition A and Preparation Condition B with Each Other]

The controller 500 outputs an analysis result including the number of blood cells in each type of white blood cell on the basis of the result of the comparison between the distribution shape of blood cells, in the X-axis or the Y-axis, of a predetermined cluster existing in a scattergram obtained under preparation condition A and the distribution shape of blood cells, in the X-axis or the Y-axis, of the predetermined cluster existing in a scattergram obtained under preparation condition B.

More specifically, if the number of peaks included in the distribution shape of blood cells, in the X-axis or the Y-axis, of a predetermined cluster existing in a scattergram obtained under preparation condition A and the number of peaks included in the distribution shape of blood cells, in the X-axis or the Y-axis, of the predetermined cluster existing in a scattergram obtained under preparation condition B are equal to each other, or if the number of peaks is larger under preparation condition B than under preparation condition A, the controller 500 determines that the white blood cells have been sufficiently classified under preparation condition A, and proceeds to the processing procedure of step S106. Meanwhile, if the number of peaks decreases and the number of clusters increases, the controller 500 determines that the white blood cells have been more appropriately classified in the result of the classification under preparation condition B than in the result of the classification under preparation condition A, and proceeds to the processing procedure of step S107.

The predetermined cluster used for determining the number of peaks may be any of a cluster of lymphocytes, a cluster of monocytes, a cluster of neutrophils, a cluster of eosinophils, and a cluster of basophils. Alternatively, one cluster (for example, a cluster of neutrophils) may be set in advance.

Figure 14A:
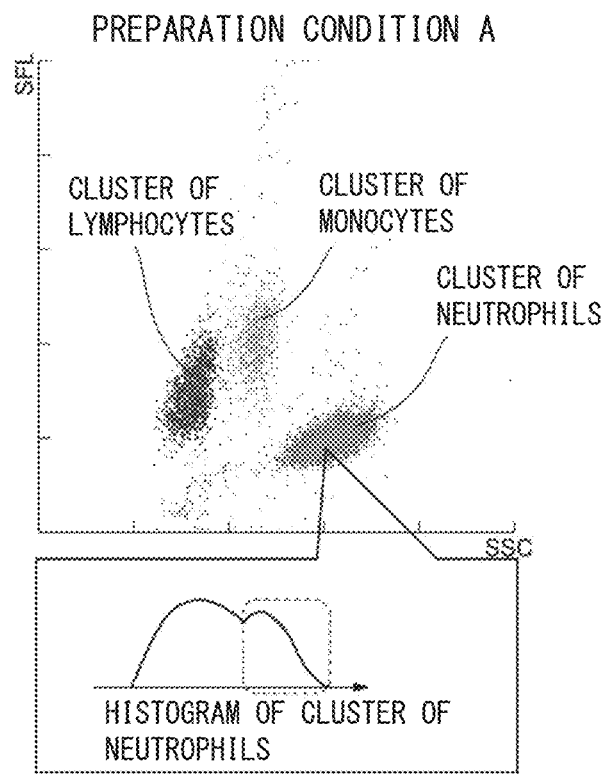
FIG. 14A illustrates an example of the result of classification under preparation condition A.
Figure 14B:
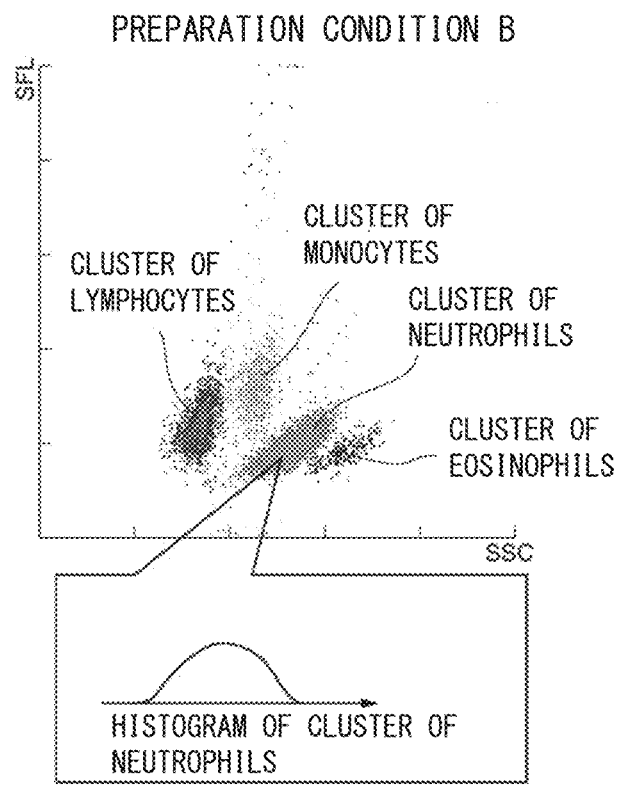
FIG. 14B illustrates an example of the result of classification under preparation condition B.
Figure 15A:
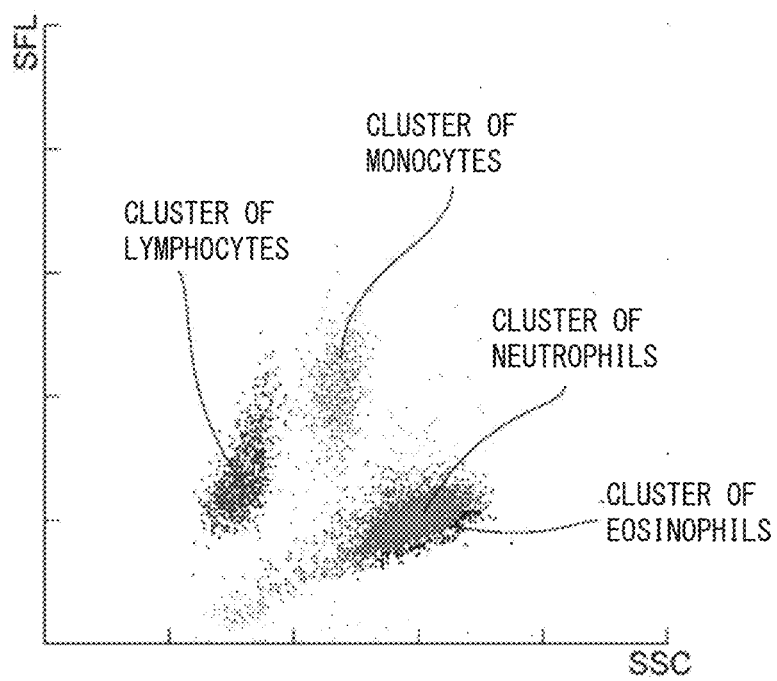
FIG. 15A illustrates an example of the result of classification under preparation condition A.
Figure 15B:
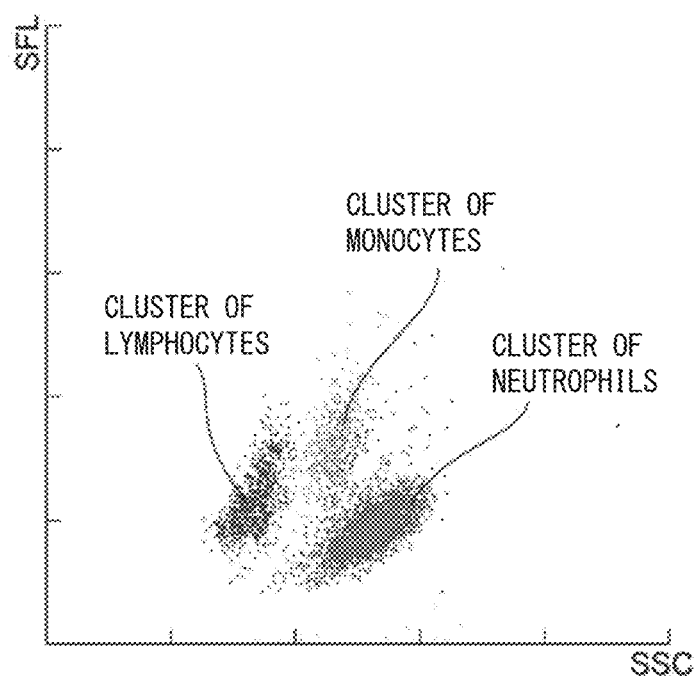
FIG. 15B illustrates an example of the result of classification under preparation condition B.

FIG. 14A illustrates an example of the result of the classification under preparation condition A, and FIG. 14B illustrates an example of the result of the classification under preparation condition B. In the examples in FIG. 14A and FIG. 14B, two peaks exist in a cluster of neutrophils in the case of preparation condition A, but only one peak exists in the cluster of neutrophils in the case of preparation condition B. Further, the number of clusters under preparation condition A is three, but the number of clusters under preparation condition B is four. Therefore, the controller 500 determines that the white blood cells have been more appropriately classified in the result of the classification under preparation condition B than in the result of the classification under preparation condition A.

(Pattern F)

Pattern F is a method in which the number of clusters existing in a scattergram and the number of boundary particles are used to perform determination or comparison for the results of classification of white blood cells.

[Processing of Comparing Classification Results Under Preparation Condition A and Preparation Condition B with Each Other]

The controller 500 outputs an analysis result including the number of blood cells in each type of white blood cell on the basis of the result of the comparison between the number of clusters existing in a scattergram obtained under preparation condition A and the number of boundary particles in a predetermined one of the clusters; and the number of clusters existing in a scattergram obtained under preparation condition B and the number of boundary particles in the predetermined cluster.

More specifically, if the number of clusters existing in a scattergram obtained under preparation condition A is different from the number of clusters existing in a scattergram obtained under preparation condition B, or if the number of boundary particles in a predetermined cluster under preparation condition B is equal to or larger than the number of boundary particles in the predetermined cluster under preparation condition A, the controller 500 determines that the white blood cells have been sufficiently classified under preparation condition A, and proceeds to the processing procedure of step S106.

Meanwhile, if the number of clusters existing in the scattergram obtained under preparation condition A is equal to the number of clusters existing in the scattergram obtained under preparation condition B, and the number of boundary particles in the predetermined cluster under preparation condition B is smaller than the number of boundary particles in the predetermined cluster under preparation condition A, the controller 500 determines that the white blood cells have been more appropriately classified in the result of the classification under preparation condition B than in the result of the classification under preparation condition A, and proceeds to the processing procedure of step S107.

In pattern F, "the number of boundary particles in a predetermined cluster" means the number of blood cells that exist on a boundary portion in the predetermined cluster and that are of a type different from that of the predetermined cluster. Specifically, there is a case where, in a scattergram in which the side fluorescence signal (SFL) and the side scattered light signal (SSC) are used, blood cells that can be classified as eosinophils when the forward scattered light signal (FSC) is taken into account exist among blood cells existing on the right-side boundary portion of the cluster of neutrophils, for example. In such a case, the counted number of the blood cells that can be classified as eosinophils corresponds to "the number of boundary particles in the predetermined cluster".

The reason why the result of the classification under preparation condition B has been determined to be more appropriate in pattern F even though the number of boundary particles has decreased, is because the counted number obtained under preparation condition A is considered to be erroneous (for example, blood cells have been counted as eosinophils even though the blood cells are neutrophils).
(Pattern G)

Pattern G is a method in which the width of a predetermined cluster and the number of clusters existing in a scattergram are used to perform determination or comparison for the results of classification of white blood cells.
[Processing of Comparing Classification Results Under Preparation Condition A and Preparation Condition B with Each Other]

The controller 500 outputs an analysis result including the number of blood cells in each type of white blood cell on the basis of the result of the comparison between the width of a predetermined cluster and the number of clusters existing in a scattergram obtained under preparation condition A; and the width of the predetermined cluster and the number of clusters existing in a scattergram obtained under preparation condition B.

More specifically, if the width of a predetermined cluster existing in a scattergram obtained under preparation condition B is equal to or longer than the width of the predetermined cluster existing in a scattergram obtained under preparation condition A, or if the number of clusters under preparation condition B is equal to or smaller than the number of clusters under preparation condition A, the controller 500 determines that the white blood cells have been sufficiently classified under preparation condition A, and proceeds to the processing procedure of step S106.

If the width of the predetermined cluster existing in the scattergram obtained under preparation condition B is shorter than the width of the predetermined cluster existing in the scattergram obtained under preparation condition A, and the number of clusters under preparation condition B is larger than the number of clusters under preparation condition A, the controller 500 determines that the white blood cells have been more appropriately classified in the result of the classification under preparation condition B than in the result of the classification under preparation condition A, and proceeds to the processing procedure of step S107.

Figure 16A:
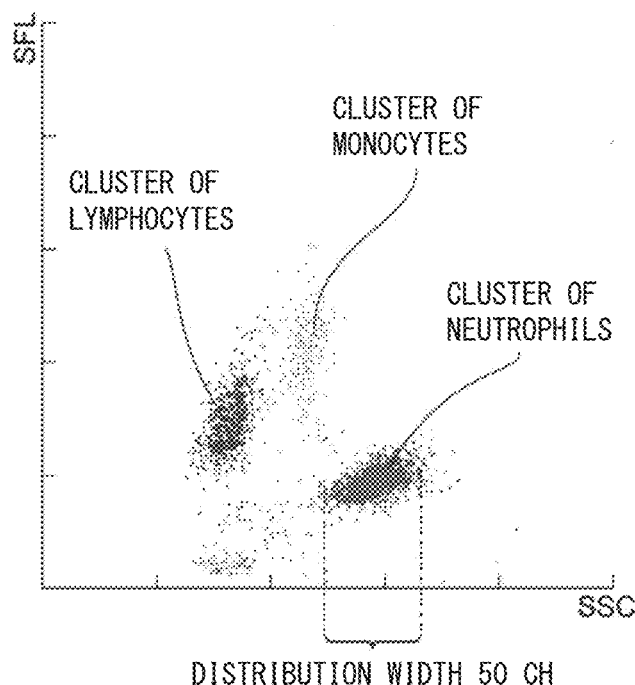
FIG. 16A illustrates an example of the result of classification under preparation condition A.
Figure 16B:
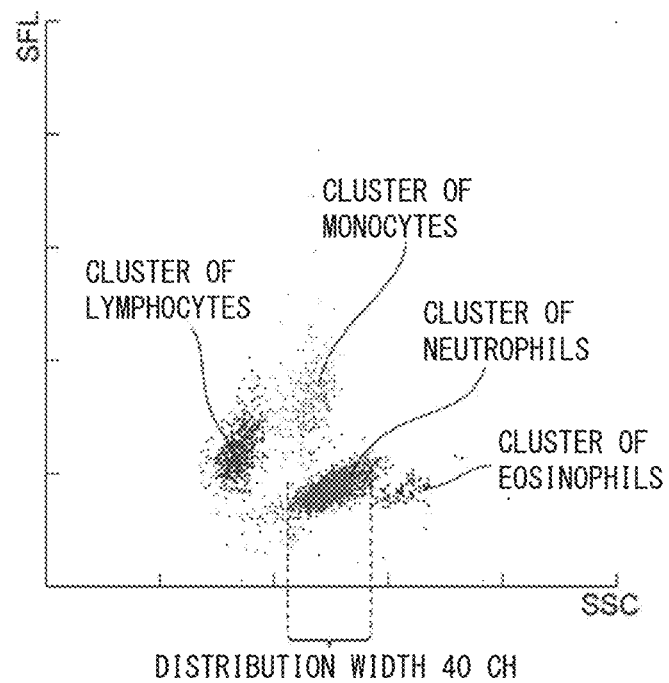
FIG. 16B illustrates an example of the result of classification under preparation condition B.

FIG. 16A illustrates an example of the result of the classification under preparation condition A, and FIG. 16B illustrates an example of the result of the classification under preparation condition B. In the examples in FIG. 16A and FIG. 16B, the width of a cluster of neutrophils under preparation condition A is 50 channels, but the width of the cluster of neutrophils under preparation condition B is 40 channels. Further, the number of clusters under preparation condition A is three, but the number of clusters under preparation condition B is four. Therefore, the controller 500 determines that the white blood cells have been more appropriately classified in the result of the classification under preparation condition B than in the result of the classification under preparation condition A.

The width of the cluster may be a width in the X-axis or a width in the Y-axis. The width of the cluster may be a width, in the X-axis (or Y-axis), that includes channels in each of which the number of blood cells existing in the channel is equal to or larger than a predetermined number.

The scattergram under preparation condition A and the scattergram under preparation condition B described above are referred to as a first distribution chart and a second distribution chart, respectively.

Regarding the processing procedure of step S105, the result of the classification of white blood cells performed by using light signals obtained under preparation condition A may be expressed as at least one of "the number of white blood cells belonging to one cluster among a plurality of clusters included in a scattergram under preparation condition A", "the number of a plurality of clusters included in a scattergram under preparation condition A", "the distance between two clusters included in a scattergram under preparation condition A", "the extent to which the boundaries of two clusters included in a scattergram under preparation condition A are in contact with each other", and "the width of a predetermined cluster among a plurality of clusters included in a scattergram under preparation condition A".

Regarding the processing procedure of step S105, the result of the classification of white blood cells performed by using light signals obtained under preparation condition B may be expressed as at least one of "the number of white blood cells belonging to one cluster among a plurality of clusters included in a scattergram under preparation condition B", "the number of a plurality of clusters included in a scattergram under preparation condition B", "the distance between two clusters included in a scattergram under preparation condition B", "the extent to which the boundaries of two clusters included in a scattergram under preparation condition B are in contact with each other", and "the width of a predetermined cluster among a plurality of clusters included in a scattergram under preparation condition B".

Regarding the processing procedure of step S105, the result of the comparison between the result of the classification under preparation condition A and the result of the classification under preparation condition B may be expressed as at least one of "the result of the comparison between the number of white blood cells belonging to the one cluster among the plurality of clusters included in the scattergram under preparation condition A and the number of white blood cells belonging to the one cluster among the plurality of clusters included in the scattergram under preparation condition B", "the result of the comparison between the number of the plurality of clusters included in the scattergram under preparation condition A and the number of the plurality of clusters included in the scattergram under preparation condition B", "the result of the comparison between the distance between the two clusters included in the scattergram under preparation condition A and the distance between the two clusters included in the scattergram under preparation condition B", "the result of the comparison between the extent to which the boundaries of the two clusters included in the scattergram under preparation condition A are in contact with each other and the extent to which the boundaries of the two clusters included in the scattergram under preparation condition B are in contact with each other", and "the result of the comparison between the width of the predetermined cluster among the plurality of clusters included in the scattergram under preparation condition A and the width of the predetermined cluster among the plurality of clusters included in the scattergram under preparation condition B".

CONCLUSION

According to the above-described embodiment, a blood specimen having been subjected to preparation on the basis of preparation condition A is measured in the normal mode. If determination that white blood cells may not have been sufficiently classified in the normal mode is made, transition is made to the extension mode in which classification of white blood cells is performed on both of the blood specimen having been subjected to preparation on the basis of preparation condition A and the blood specimen having been subjected to preparation on the basis of preparation condition B. In addition, both results of classification are compared with each other, and an analysis result including the result of the comparison is outputted. This makes it possible to inhibit an analysis result with an insufficient accuracy from being outputted depending on the property of the specimen.

In the above-described embodiment, an example in which neutrophils and eosinophils are classified under the two types of preparation conditions has been described. However, the present disclosure is not limited to the example. For example, the present disclosure may be applied to an example in which neutrophils and monocytes are classified by using the side fluorescence signal (SFL) and the side scattered light signal (SSC). In this case, the reaction time for a specimen and a reagent under the preparation condition in step S104 shown in FIG. 9 may be set to be shorter than the reaction time for the specimen and the reagent under the preparation condition in step S103 shown in FIG. 9. Similarly, the reaction temperature under the preparation condition in step S104 may be set to be lower than the reaction temperature under the preparation condition in step S103, or the mixing ratio of the reagent under the preparation condition in step S104 may be set to be lower than the mixing ratio of the reagent under the preparation condition in step S103.

The types of light signals used for classifying blood cells are not limited, and two types other than the above-described combinations may be combined with each other. Alternatively, three or more types of light signals may be combined with one another. Alternatively, one type of light signal may be used.

The type of cells to be classified under the two types of preparation conditions is also not limited to white blood cells and may be red blood cells, platelets, or other blood cells.

The above-described embodiment is not limited to analysis of a blood specimen and is applicable also to analysis of various body fluids other than blood and urine. In this case, in the above description, the term "white blood cell" may be replaced with the term "cell". In addition, for example, an analyzer 1 for analyzing urine may be configured to classify red blood cells, white blood cells, epithelial cells, squamous epithelial cells, casts, and bacteria contained in urine and count the number of each of the classified types.

The above-described embodiment is not limited to a mode in which light is applied to a first measurement sample and a second measurement sample; and light signals are obtained. For example, the present disclosure may be applied to a cell analyzer configured to obtain electrical signals generated when the first measurement sample and the second measurement sample pass through a small hole to which voltage has been applied; and classify cells by using the obtained electrical signals. In this case, in the above description, the "first light signal" may be referred to as a "first signal", the "second light signal" may be referred to as a "second signal", and the "third light signal" may be referred to as a "third signal".

The above-described embodiment is for facilitating understanding of the present disclosure, and is not for limiting the present disclosure. The flow charts, sequences, and elements of the embodiment, and the arrangements, materials, conditions, shapes, sizes, etc., thereof described in the embodiment are not limited to those which are shown as examples, and can be changed as appropriate. Components shown in different embodiments can be partially replaced with each other, or can be combined with each other.

What is claimed is:

1. A cell classification method, to be executed by an analyzer, for classifying cells contained in a specimen, the cell classification method comprising:
preparing a first measurement sample by treating a specimen under a first preparation condition;
obtaining a first signal from the prepared first measurement sample;
classifying, by using the first signal, cells contained in the first measurement sample;
preparing a second measurement sample by treating the specimen under a second preparation condition different from the first preparation condition;
obtaining a second signal from the prepared second measurement sample;
classifying, by using the second signal, cells contained in the second measurement sample; and
comparing a result of the cell classification performed by using the first signal and a result of the cell classification performed by using the second signal, with each other, and outputting an analysis result including a number of cells on the basis of a result of the comparison.

2. The cell classification method of claim 1, wherein the outputting of the analysis result includes:
outputting a number of cells that is based on the first signal, if the result of the comparison is within a predetermined range; and outputting the number of cells that is based on the first signal and information about a reliability of the number of cells, if the result of the comparison is outside the predetermined range.

3. The cell classification method of claim 1, wherein the outputting of the analysis result includes:
outputting a number of cells that is based on the first signal, if the result of the comparison is within a predetermined range; and
outputting a number of cells that is based on the second signal, if the result of the comparison is outside the predetermined range.

4. The cell classification method of claim 1, further comprising receiving a measurement instruction for a specimen, wherein
upon reception of the measurement instruction,
the preparing of the first measurement sample,
the obtaining of the first signal,
the classifying of the cells by using the first signal,
the preparing of the second measurement sample,
the obtaining of the second signal,
the classifying of the cells by using the second signal, and
the outputting of the analysis result,
are executed.

5. The cell classification method of claim 1, further comprising:
preparing a third measurement sample by treating the specimen under the first preparation condition;
obtaining a third signal from the prepared third measurement sample; and
classifying, by using the third signal, cells contained in the third measurement sample, wherein
if a result of the cell classification performed by using the third signal satisfies a predetermined condition,
the preparing of the first measurement sample,
the obtaining of the first signal,
the classifying of the cells contained in the first measurement sample,
the preparing of the second measurement sample,
the obtaining of the second signal,
the classifying of the cells contained in the second measurement sample, and
the outputting of the analysis result,
are executed.

6. The cell classification method of claim 1, wherein
each of the first and second preparation conditions is at least one condition among: a condition regarding a time length during which a reagent is reacted with the specimen; a condition regarding a temperature when a reagent is reacted with the specimen; and a condition regarding a mixing ratio between the specimen and a reagent.

7. The cell classification method of claim 1, wherein
the first signal is a first light signal,
the obtaining of the first signal includes applying light to the first measurement sample, to obtain the first light signal,
the second signal is a second light signal, and
the obtaining of the second signal includes applying light to the second measurement sample, to obtain the second light signal.

8. The cell classification method of claim 7, wherein
the first light signal includes at least two light signals among two types of scattered lights each having a different angle and fluorescence which are emitted from the first measurement sample,
the second light signal includes at least two light signals among two types of scattered lights each having a different angle and fluorescence which are emitted from the second measurement sample,
a result of cell classification performed by using the first light signal is obtained on the basis of a first distribution chart obtained by plotting, in different axes, the at least two light signals included in the first light signal, and
a result of cell classification performed by using the second light signal is obtained on the basis of a second distribution chart obtained by plotting, in different axes, the at least two light signals included in the second light signal.

9. The cell classification method of claim 8, wherein
the result of the cell classification performed by using the first light signal is at least one of
a number of cells belonging to one cluster among a plurality of clusters included in the first distribution chart,
a number of a plurality of clusters included in the first distribution chart,
a distance between two clusters included in the first distribution chart,
an extent to which boundaries of two clusters included in the first distribution chart are in contact with each other, and
a width of a predetermined cluster among a plurality of clusters included in the first distribution chart,
the result of the cell classification performed by using the second light signal is at least one of
a number of cells belonging to one cluster among a plurality of clusters included in the second distribution chart,
a number of a plurality of clusters included in the second distribution chart,
a distance between two clusters included in the second distribution chart,
an extent to which boundaries of two clusters included in the second distribution chart are in contact with each other, and
a width of a predetermined cluster among a plurality of clusters included in the second distribution chart, and
the result of the comparison is at least one of
a result of comparison between the number of cells belonging to the one cluster among the plurality of clusters included in the first distribution chart and the number of cells belonging to the one cluster among the plurality of clusters included in the second distribution chart,
a result of comparison between the number of the plurality of clusters included in the first distribution chart and the number of the plurality of clusters included in the second distribution chart,
a result of comparison between the distance between the two clusters included in the first distribution chart and the distance between the two clusters included in the second distribution chart,
a result of comparison between the extent to which the boundaries of the two clusters included in the first distribution chart are in contact with each other and the extent to which the boundaries of the two clusters included in the second distribution chart are in contact with each other, and
a result of comparison between the width of the predetermined cluster among the plurality of clusters included in the first distribution chart and the width of the predetermined cluster among the plurality of clusters included in the second distribution chart.

10. The cell classification method of claim 1, wherein the specimen is blood, and
the cells to be classified include at least lymphocytes, monocytes, neutrophils, and eosinophils.

11. The cell classification method of claim 1, wherein the first signal and the second signal are obtained by a same detector.

12. The cell classification method of claim 1, wherein the first signal is obtained from the first measurement sample flowing through a flow cell, and
the second signal is obtained from the second measurement sample flowing through the flow cell.

13. A cell classification method, to be executed by an analyzer, for classifying cells contained in a specimen, the cell classification method comprising:
preparing a first measurement sample by treating a specimen under a first preparation condition;
obtaining a first signal from the prepared first measurement sample;
classifying, by using the first signal, cells contained in the first measurement sample;
evaluating classification performance of the cell classification performed by using the first signal; and
if a result of the evaluation of the classification performance satisfies a predetermined condition,
preparing a second measurement sample by treating the specimen under a second preparation condition different from the first preparation condition,
obtaining a second signal from the prepared second measurement sample,
classifying, by using the second signal, cells contained in the second measurement sample, and
outputting a number of cells that is based on the second signal.

14. A cell classification method, to be executed by an analyzer, for classifying cells contained in a specimen, the cell classification method comprising:
preparing a first measurement sample by treating a specimen under a first preparation condition;
obtaining a first signal from the prepared first measurement sample;
classifying, by using the first signal, cells contained in the first measurement sample;
preparing a second measurement sample by treating the specimen under a second preparation condition different from the first preparation condition;
obtaining a second signal from the prepared second measurement sample;
classifying, by using the second signal, cells contained in the second measurement sample;
evaluating classification performance of the cell classification performed by using the first signal; and
outputting, on the basis of a result of the evaluation of the classification performance, an analysis result including a number of cells that is based on the first signal or an analysis result including a number of cells that is based on the second signal.

15. An analyzer configured to classify cells contained in a specimen, the analyzer comprising:
a sample preparation part comprising a mixing chamber and configured to generate a measurement sample by preparation from a specimen with a reagent in the mixing chamber;
a detector comprising a flow cell in which the measurement sample flows and configured to obtain a signal from the measurement sample flowing in the flow cell; and
a controller comprising a memory storing a computer program and a processor to execute the computer program, wherein
the controller is programmed to execute
causing the sample preparation part to execute
preparing a first measurement sample by treating a specimen under a first preparation condition and
preparing a second measurement sample by treating the specimen under a second preparation condition different from the first preparation condition,
causing the detector to execute
obtaining a first signal from the prepared first measurement sample and
obtaining a second signal from the prepared second measurement sample,
classifying, by using the first signal, cells contained in the specimen,
classifying, by using the second signal, cells contained in the specimen, and
comparing a result of the cell classification performed by using the first signal and a result of the cell classification performed by using the second signal, with each other, and outputting an analysis result on the basis of a result of the comparison.

16. An analyzer configured to classify cells contained in a specimen, the analyzer comprising:
a sample preparation part comprising a mixing chamber and configured to generate a measurement sample by preparation from a specimen with a reagent in the mixing chamber;
a detector comprising a flow cell in which the measurement sample flows and configured to obtain a signal from the measurement sample flowing in the flow cell; and
a controller comprising a memory storing a computer program and a processor to execute the computer program, wherein
the controller is programmed to execute
causing the sample preparation part to execute
preparing a first measurement sample by treating a specimen under a first preparation condition and
preparing a second measurement sample by treating the specimen under a second preparation condition different from the first preparation condition,
causing the detector to execute obtaining a first signal from the prepared first measurement sample,
classifying, by using the first signal, cells contained in the specimen,
evaluating classification performance of the cell classification performed by using the first signal, and
if a result of the evaluation of the classification performance satisfies a predetermined condition,
causing the sample preparation part to execute preparing a second measurement sample by treating the specimen under the second preparation condition different from the first preparation condition,
causing the detector to execute obtaining a second signal from the prepared second measurement sample,
classifying, by using the second signal, cells contained in the second measurement sample, and
outputting a number of cells that is based on the second signal.

17. An analyzer configured to classify cells contained in a specimen, the analyzer comprising:
- a sample preparation part comprising a mixing chamber and configured to generate a measurement sample by preparation from a specimen with a reagent in the mixing chamber;
- a detector comprising a flow cell in which the measurement sample flows and configured to obtain a signal from the measurement sample flowing in the flow cell; and
- a controller comprising a memory storing a computer program and a processer to execute the computer program, wherein the controller is programmed to execute
causing the sample preparation part to execute
preparing a first measurement sample by treating a specimen under a first preparation condition and
preparing a second measurement sample by treating the specimen under a second preparation condition different from the first preparation condition,
causing the detector to execute
obtaining a first signal from the prepared first measurement sample and
obtaining a second signal from the prepared second measurement sample,
classifying, by using the first signal, cells contained in the specimen,
classifying, by using the second signal, cells contained in the specimen,
evaluating classification performance of the cell classification performed by using the first signal, and
outputting, on the basis of a result of the evaluation of the classification performance, an analysis result including a number of cells that is based on the first signal or an analysis result including a number of cells that is based on the second signal.

18. A program stored on a non-transitory computer readable medium configured to cause a computer to execute:
causing a sample preparation part, which is configured to generate a measurement sample by preparation from a specimen with a reagent, to execute
preparing a first measurement sample by treating a specimen under a first preparation condition and
preparing a second measurement sample by treating the specimen under a second preparation condition different from the first preparation condition;
causing a detector, which is configured to obtain a signal from a measurement sample, to execute
obtaining a first signal from the prepared first measurement sample and
obtaining a second signal from the prepared second measurement sample;
classifying, by using the first signal, cells contained in the specimen;
classifying, by using the second signal, cells contained in the specimen; and
comparing a result of the cell classification performed by using the first signal and a result of the cell classification performed by using the second signal, with each other, and outputting an analysis result on the basis of a result of the comparison.

19. A program stored on a non-transitory computer readable medium configured to cause a computer to execute:
causing a sample preparation part, which is configured to generate a measurement sample by preparation from a specimen with a reagent, to execute
preparing a first measurement sample by treating a specimen under a first preparation condition and
preparing a second measurement sample by treating the specimen under a second preparation condition different from the first preparation condition;
causing a detector, which is configured to obtain a signal from a measurement sample, to execute obtaining a first signal from the prepared first measurement sample;
evaluating classification performance of the cell classification performed by using the first signal; and
if a result of the evaluation of the classification performance satisfies a predetermined condition,
causing the sample preparation part to execute preparing a second measurement sample by treating the specimen under the second preparation condition different from the first preparation condition,
causing the detector to execute obtaining a second signal from the prepared second measurement sample,
classifying, by using the second signal, cells contained in the second measurement sample, and
outputting a number of cells that is based on the second signal.

20. A program stored on a non-transitory computer readable medium configured to cause a computer to execute:
causing a sample preparation part, which is configured to generate a measurement sample by preparation from a specimen with a reagent, to execute
preparing a first measurement sample by treating a specimen under a first preparation condition and
preparing a second measurement sample by treating the specimen under a second preparation condition different from the first preparation condition;
causing a detector, which is configured to obtain a signal from a measurement sample, to execute
obtaining a first signal from the prepared first measurement sample and
obtaining a second signal from the prepared second measurement sample;
classifying, by using the first signal, cells contained in the specimen;
classifying, by using the second signal, cells contained in the specimen;
evaluating classification performance of the cell classification performed by using the first signal; and
outputting, on the basis of a result of the evaluation of the classification performance, an analysis result including a number of cells that is based on the first signal or an analysis result including a number of cells that is based on the second signal.

* * * * *